(12) United States Patent
Moon et al.

(10) Patent No.: US 6,693,126 B2
(45) Date of Patent: Feb. 17, 2004

(54) DIHYDROXYPHENYL DERIVATIVES FOR HEPATOPROTECTION AND TREATMENT OF LIVER DISEASES

(75) Inventors: Sung-Hwan Moon, Kyunggi-do (KR); Hea-Jin Choi, Kyunggi-do (KR); Su-Jin Lee, Kyunggi-do (KR); Jea-Uk Chung, Kyunggi-do (KR); Jong-Ryul Ha, Kyunggi-do (KR); Kwang-Won Jeong, Kyunggi-do (KR); Se-Woong Oh, Kyunggi-do (KR)

(73) Assignee: Choongwae Pharm. Co., Ltd., Seoul (KR)

( * ) Notice: Subject to any disclaimer, the term of this patent is extended or adjusted under 35 U.S.C. 154(b) by 55 days.

(21) Appl. No.: 10/114,007

(22) Filed: Apr. 1, 2002

(65) Prior Publication Data

US 2003/0083326 A1 May 1, 2003

Related U.S. Application Data

(63) Continuation-in-part of application No. 09/674,187, filed on Oct. 27, 2000, now abandoned.

(51) Int. Cl.$^7$ .......................... A61R 31/05; A61R 31/38
(52) U.S. Cl. ...................................... 514/464; 514/640
(58) Field of Search ................... 514/464, 640

(56) References Cited

FOREIGN PATENT DOCUMENTS

| DE | 24 28 680 | 6/1974 |
|----|-----------|--------|
| DE | 24 38 399 | 8/1974 |
| EP | 0 488 144 | 6/1992 |
| JP | 56/057712 | * 5/1981 |

OTHER PUBLICATIONS

Macchia et al., *IL FARMACO* 49(12) 767–773 (1994).

* cited by examiner

*Primary Examiner*—Robert Gerstl
(74) *Attorney, Agent, or Firm*—Peter F. Corless; John B. Alexander; Edwards & Angell, LLP

(57) ABSTRACT

The present invention relates to a pharmaceutical composition for the hepatoprotection and treatment of liver diseases comprising as an active ingredient a dihydroxyphenyl derivative represented by the following formula (1), pharmaceutically acceptable acid addition salt or stereochemical isomer thereof together with a pharmaceutically acceptable inert carrier:

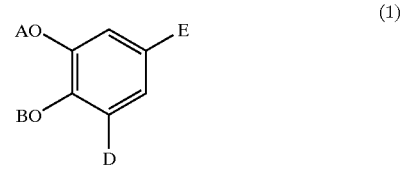

(1)

in which in which

A, B, D and E are defined as described in the specification.

3 Claims, No Drawings

DIHYDROXYPHENYL DERIVATIVES FOR HEPATOPROTECTION AND TREATMENT OF LIVER DISEASES

This application is a continuation-in-part of Ser. No. 09/674,187 filed on Oct. 27, 2000 now abandoned as Dihydroxyphenyl derivatives for hepatoprotection and treatment of liver diseases.

BACKGROUND OF THE INVENTION

1. Field of the Invention

The present invention relates to a composition for hepatoprotection and treatment of liver diseases comprising a dihydroxyphenyl derivative represented by the following formula (1) which has an excellent hepatoprotective and therapeutic activity for liver diseases:

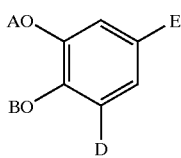

(1)

in which
A and B independently of one another represent hydrogen, or together represent methylene group,
D represents hydrogen or lower alkoxy,
E represents acetylthioacetyl, or represents the following substituent (a-1) or (a-2):

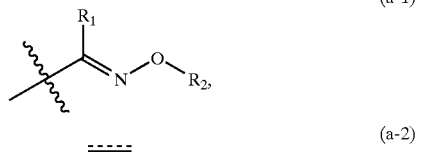

(a-1)

(a-2)

wherein
===== represents single or double bond,
$R_1$ represents hydrogen, lower alkyl or N-acetylmethylaminomethyl,
$R_2$ represents hydrogen, or represents lower alkyl which is optionally substituted by hydroxycarbonyl, phenyl or 5- or 6-membered heteroaryl containing one or more hetero atoms selected from a group consisting of nitrogen and sulfur, wherein the heteroaryl can be substituted by lower alkyl,
$R_3$ represents hydrogen, hydroxycarbonyl, lower alkoxycarbonyl, lower alkylcarbamoyl or lower alkenylcarbamoyl, or represents lower alkyl which is substituted by hydroxy, aryl(lower)alkoxy or 5- or 6-membered heteroaryl(lower)alkoxy containing nitrogen as the hetero atom,
$R_4$ represents hydrogen, or represents lower alkanoyl which is optionally substituted by halogen,
provided that $R_4$ does not exist when double bond is linked to the nitrogen atom in substituent (a-2).

The present invention also relates to a novel dihydroxyphenyl derivative having an excellent protective and therapeutic acitivity for liver which is left after known compounds are removed from the compound of formula (1) above, and to a process for preparing the same.

2. Description of the Prior Art

The liver has been known as an important organ wherein various metabolic activities are carried out. Acute or chronic lesions can be developed by a variety of factors including noxious materials such as virus, chemicals, etc., and undernourishment, which may cause liver injuries such as fatty liver, hepatitis, jaundice, cirrhotic liver, hepatic sclerosis, and liver cancer, etc. Recently, as the therapeutic agents for liver diseases, silymarin(see, Biotech, Therapeutics, 1993, 4, 263–270), malotilate(see, Japan, J. Exp. Med., 1986, 56, 235–245; Biochem, Biophy. Res. Comm., 1994, 200, 1414, 1994), DDB(see, Biochem. Biophy. Res. Comm., 1981, 103, 1131–1137), flumecinol(see, U.S. Pat. No. 4,039,589), etc. were reported, and yet which also have been proved to have demerits of their own. That is, silymarin has a low bioavailability and medicinal effect; malotilate exhibits a hematotoxicity and low bioavailability in oral administration and further it causes undesirable side effects due to its metabolite; flumecinol can be restrictively used to an infant; and DDB has a low bioavailability when administered orally. In addition, a dietary cure, symptomatic treatment, and medical therapies using steroids, immune-related agent, etc. are known, but the efficacy thereof as a therapeutic agent is immaterial. Further, the present inventors have identified the therapeutic effect of novel genipin derivatives to hepatitis.

While, the following compounds of formulas (2) to (4) may be mentioned as reference compounds having a similar structure to that of the compound of formula (1) according to the present invention and also similar use. First, the thiazofuran of formula (2) as a thiazole derivative acts as an inhibitor for purine biosynthesis, by which it exhibits a therapeutic effect to myelocytic leukemia. Therefore, it is now in a third clinical test by ICN company.

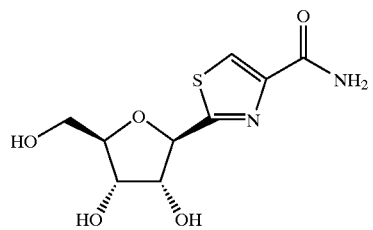

(2)

Also, the thiazoline derivative of the following formula (3) has been reported to have parasiticidal and fungicidal effects(see, Pharm. Acta. Helv. 1991, 66(8), 237–40), and the pidotimod of the following formula (4) which is a thiazolidine derivative has been marketed by Poli Industria Chimica since 1993 as an immuno-regulatory agent through the mechanism of PNP(purine nucleoside phosphorylase) inhibition.

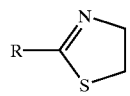

(3)

in which
R represents phenyl, substituted phenyl, 2-furyl, 1-naphthyl or 4-pyridyl.

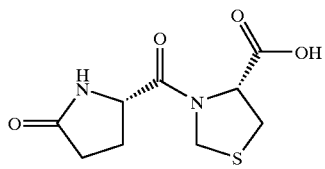

(4)

DISCLOSURE OF INVENTION

Under such a technical background as mentioned above, the present inventors have extensively studied to develop novel compounds which can be effectively used in the hepatoprotection and treatment of liver diseases. As a result, we have succeeded to identify that the compound of formula (1) according to the present invention exhibits a potent hepatoprotective and therapeutic activity for liver diseases, and further part of the compound of formula (1) is novel.

Therefore, it is an object of the present invention to provide a pharmaceutical composition for the hepatoprotection and treatment of liver diseases comprising as an active ingredient a dihydroxyphenyl derivative of formula (1), as defined below, pharmaceutically acceptable acid addition salt or stereochemical isomer thereof together with a pharmaceutically acceptable inert carrier.

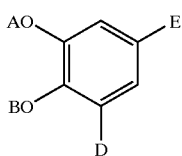

(1)

in which

A and B independently of one another represent hydrogen, or together represent methylene group, D represents hydrogen or lower alkoxy, E represents acetylthioacetyl, or represents the following substituent (a-1) or (a-2):

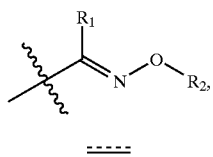

(a-1)

----- (a-2)

wherein

===== represents single or double bond, $R_1$ represents hydrogen, lower alkyl or N-acetylmethylaminomethyl, $R_2$ represents hydrogen, or represents lower alkyl which is optionally substituted by hydroxycarbonyl, phenyl or 5- or 6-membered heteroaryl containing one or more hetero atoms selected from a group consisting of nitrogen and sulfur, wherein the heteroaryl can be substituted by lower alkyl, $R_3$ represents hydrogen, hydroxycarbonyl, lower alkoxycarbonyl, lower alkylcarbamoyl or lower alkenylcarbamoyl, or represents lower alkyl which is substituted by hydroxy, aryl(lower)alkoxy or 5- or 6-membered heteroaryl(lower)alkoxy containing nitrogen as the hetero atom, $R_4$ represents hydrogen, or represents lower alkanoyl which is optionally substituted by halogen, provided that $R_4$ does not exist when double bond is linked to the nitrogen atom in substituent (a-2).

Part of the compound of formula (1) which is left after known compounds are removed therefrom is novel, and therefore it is another object of the present invention to provide such a novel dihydroxyphenyl derivative and processes for the preparation thereof.

The novel dihydroxyphenyl derivative according to the present invention is the compound of formula (1) wherein A and B independently of one another represent hydrogen, or together represent methylene group, D represents hydrogen or lower alkoxy, E represents acetylthioacetyl, or represents the following substituent (a-1) or (a-2):

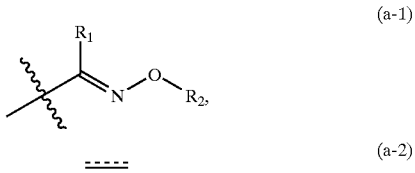

(a-1)

----- (a-2)

wherein

===== represents single or double bond, $R_1$ represents hydrogen, lower alkyl or N-acetylmethylaminomethyl, $R_2$ represents hydrogen, or represents lower alkyl which is optionally substituted by hydroxycarbonyl, phenyl or 5- or 6-membered heteroaryl containing one or more hetero atoms selected from a group consisting of nitrogen and sulfur, wherein the heteroaryl can be substituted by lower alkyl, $R_3$ represents hydrogen, hydroxycarbonyl, lower alkoxycarbonyl, lower alkylcarbamoyl or lower alkenylcarbamoyl, or represents lower alkyl which is substituted by hydroxy, aryl(lower)alkoxy or 5- or 6-membered heteroaryl(lower)alkoxy containing nitrogen as the hetero atom, $R_4$ represents hydrogen, or represents lower alkanoyl which is optionally substituted by halogen, provided that i) $R_1$ and $R_2$ are not hydrogen or methyl when D is hydrogen and E is substituent (a-1), ii) $R_3$ is not hydrogen in the thiazoline ring of (a-2) when D is hydrogen and E is substituent (a-2), and iii) $R_4$ does not exist when double bond is linked to the nitrogen atom in substituent (a-2).

BEST MODE FOR CARRYING OUT THE INVENTION

More preferred composition according to the present invention comprises a dihydroxyphenyl derivative represented by the following formula (1):

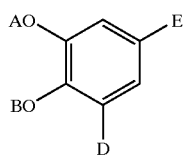

in which
A and B both represent hydrogen, or together represent a methylene group,
D represents hydrogen or $C_1$-$C_4$-alkoxy,
E represents the following substituent (a-1)

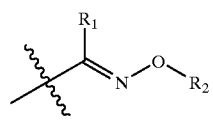

wherein
$R_1$ represents hydrogen, $C_1$-$C_4$-alkyl or N-acetylmethylaminomethyl,
$R_2$ represents hydrogen, or represents $C_1$-$C_4$-alkyl which is optionally substituted by hydroxycarbonyl, phenyl or 5- or 6-membered heteroaryl containing one or more hetero atoms selected from a group consisting of nitrogen and sulfur, wherein the heteroaryl can be substituted by $C_1$-$C_4$-alkyl,
provided that when A and B together form a methylene group, D is hydrogen, $R_1$ is hydrogen, and $R_2$ is not hydroxycarbonylethyl; and
provided that when A, B, D and $R_1$ independently are hydrogen, $R_2$ is not hydrogen.

Among the novel compound of formula (1) according to the present invention, the preferred compounds include those wherein D represents hydrogen or methoxy, E represents substituent

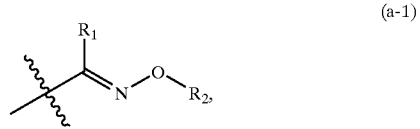

wherein $R_1$ represents hydrogen or methyl, and $R_2$ represents hydrogen, methyl, t-butyl, hydroxycarbonylmethyl, benzyl, 2-pyridylmethyl or 4-methylthiazol-5-ylethyl.

Also preferred compounds of formula (1) include those wherein D represents hydrogen or methoxy, E represents subsituent (a-2), wherein represents single or double bond, $R_3$ represents hydrogen, hydroxycarbonyl, lower alkoxycarbonyl, lower alkylcarbamoyl, lower alkenylcarbamoyl, or represents lower alkyl substituted by hydroxy, benzyloxy or 2-pyridylmethoxy, and $R_4$ represents hydrogen, or lower alkanoyl which is optionally substituted by halogen. Particularly preferred compounds among these compounds are those wherein D represents hydrogen, E represents substituent (a-2), wherein $R_3$ represents hydrogen, hydroxycarbonyl, ethoxycarbonyl, methylcarbamoyl, allylcarbamoyl, or methyl substituted by hydroxy, benzyloxy or 2-pyridylmethoxy, and $R_4$ represents hydrogen, acetyl or chloroacetyl. Most preferred one is the compound wherein $R_3$ and $R_4$ are both hydrogen on the thiazole ring.

Also, preferred compounds of formula (1) include those wherein D represents hydrogen or methoxy, and E represents acetylthioacetyl.

Typical examples of the compound of formula (1) are represented in the following table 1. Among them, all the compounds except for Compound Nos. 1 to 5 are novel.

TABLE 1a

| COM. NO. | STRUCTURE | COM. NO. | STRUCTURE |
|---|---|---|---|
| 1 | 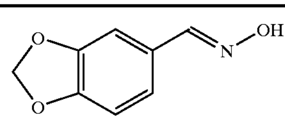 | 2 | 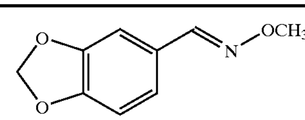 |
| 3 | 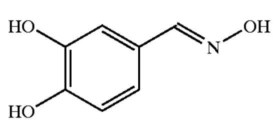 | 4 | 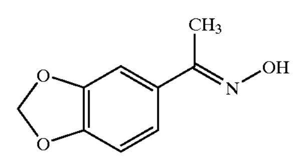 |
| 5 | 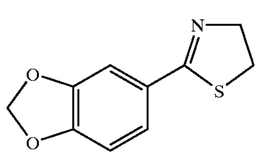 | 6 | 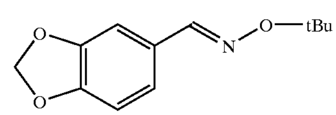 |
| 7 | 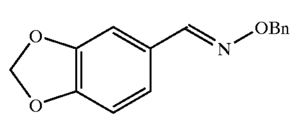 | 8 | 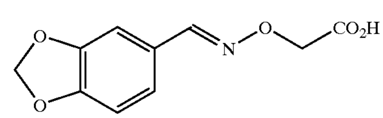 |

TABLE 1a-continued

| COM. NO. | STRUCTURE | COM. NO. | STRUCTURE |
|---|---|---|---|
| 9 | (1,3-benzodioxol-5-yl)-CH=N-O-CH2-(pyridin-2-yl) | 10 | (1,3-benzodioxol-5-yl)-CH=N-O-CH2CH2-(5-methylthiazol-2-yl) |
| 11 | 7-methoxy-1,3-benzodioxol-5-yl-CH=N-OH | 12 | 7-methoxy-1,3-benzodioxol-5-yl-CH=N-OCH3 |
| 13 | 7-methoxy-1,3-benzodioxol-5-yl-CH=N-O-CH2-(pyridin-2-yl) | 14 | 7-methoxy-1,3-benzodioxol-5-yl-CH=N-O-CH2-phenyl |

TABLE 1b

| COM. NO. | STRUCTURE | COM. NO. | STRUCTURE |
|---|---|---|---|
| 15 | 2-(1,3-benzodioxol-5-yl)-thiazolidine-4-carboxylic acid ethyl ester | 16 | 3-acetyl-2-(1,3-benzodioxol-5-yl)-thiazolidine-4-carboxylic acid ethyl ester |
| 17 | 3-chloroacetyl-2-(1,3-benzodioxol-5-yl)-thiazolidine-4-carboxylic acid ethyl ester | 18 | 2-(1,3-benzodioxol-5-yl)-4,5-dihydrothiazole-4-carboxylic acid ethyl ester |
| 19 | 2-(1,3-benzodioxol-5-yl)-4,5-dihydrothiazole-4-carboxylic acid methylamide | 20 | 2-(1,3-benzodioxol-5-yl)-4,5-dihydrothiazole-4-carboxylic acid allylamide |

TABLE 1b-continued

| COM. NO. | STRUCTURE | COM. NO. | STRUCTURE |
|---|---|---|---|
| 21 | (structure) | 22 | (structure) |
| 23 | (structure) | 24 | (structure) |

TABLE 1c

| COM. NO. | STRUCTURE | COM. NO. | STRUCTURE |
|---|---|---|---|
| 25 | (structure) | 26 | (structure) |
| 27 | (structure) | 28 | (structure) |

The compound of formula (1) according to the present invention can form a pharmaceutically acceptable salt. Such salt includes a salt with pharmaceutically acceptable acids such as asparagic acid, gluconic acid, hydrochloric acid, p-toluenesulfonic acid or citric acid, etc., a salt with bases such as pyridine or ammonia, etc., and a salt with acids or bases which are generally known and conventionally used in the technical field to which the compound of formula (1) pertains. These pharmaceutically acceptable salts can be prepared according to a conventional conversion method.

In the compound of formula (1) wherein E represents substituent (a-2), the two carbon atoms linked to the nitrogen atom on the 5-membered ring can be asymmetric, and thus the compound of formula (1) can exist as a pure stereoisomer such as enantiomer of R or S, diastereomer, etc., or a mixture thereof including racemate. Therefore, the present invention also includes each of these stereoisomers and their mixtures.

The compound of formula (1) of the present invention can be prepared according to the methods described below. However, it should be understood that the process for preparing the compound of formula (1) is not limited to those explained below since the compound can be easily prepared by optionally combining the various methods disclosed in prior arts, and such a combination may be conventionally carried out by a person having ordinary skill in the art.

According to the present invention, the novel compound of formula (1) can be prepared by processes characterized in that (a) a compound represented by the following formula (5):

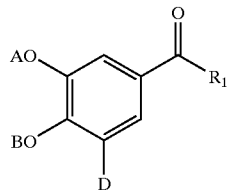
(5)

wherein A, B, D and $R_1$ are defined as previously described, is reacted with a compound represented by the following formula (6):

(6)

wherein $R_2$ is defined as previously described, in a solvent to produce a compound represented by the following formula (1a):

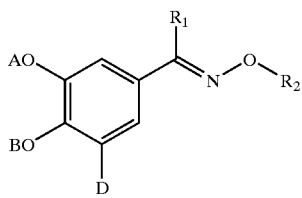
(1a)

wherein A, B, D, $R_1$ and $R_2$ are defined as previously described (see, Reaction Scheme 1);

(b) a compound represented by the following formula (7):

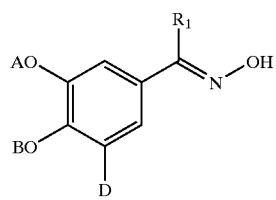
(7)

wherein A, B, D and $R_1$ are defined as previously described, is reacted with a compound represented by the following formula (8):

X-$R_2$ (8)

wherein $R_2$ is defined as previously described and X represents reactive leaving group, to produce the compound of formula (1a) (see, Reaction Scheme 2);

(c) piperonal is reacted with 1-cysteine ethylester hydrochloride in the presence of pyridine to produce a compound represented by the following formula (9):

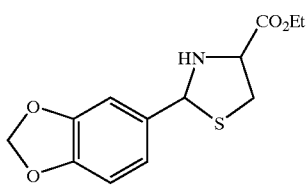
(9)

which is then reacted with lower alkanoyl halide or anhydride optionally substituted by halogen to produce a compound represented by the following formula (1b):

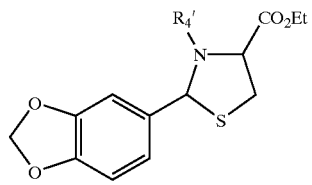
(1b)

wherein $R_4'$ represents lower alkanoyl optionally substituted by halogen (see, Reaction Scheme 3);

(d) an ethylimidate compound represented by the following formula (10):

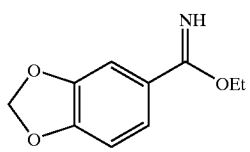
(10)

is reacted with mercaptoethylamine hydrochloride or L-cysteine (lower) alkylester hydrochloride to produce a compound represented by the following formula (1c) having a thiazoline ring:

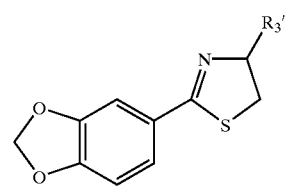
(1c)

wherein $R_3'$ represents hydrogen or lower alkoxycarbonyl (see, Reaction Scheme 4);

(e) the compound of formula (1c) is oxidized using an oxidant to produce a compound represented by the following formula (1d) having a thiazole ring:

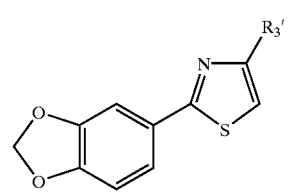
(1d)

wherein $R_3'$ is defined as previously described (see, Reaction Scheme 6);

(f) a compound represented by the following formula (11):

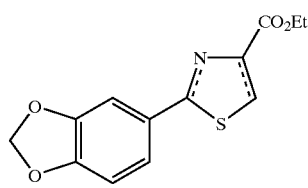
(11)

wherein ===== is defined as previously described, is reacted with lithium hydroxide, lower alkylamine or lower alkenylamine to produce a compound represented by the following formula (1e):

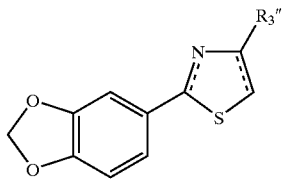

(1e)

wherein R₃″ represents hydroxycarbonyl, lower alkylcarbamoyl or lower alkenylcarbamoyl (see, Reaction Scheme 7);

(g) the compound of formula (11) is reduced to produce a compound represented by the following formula (12):

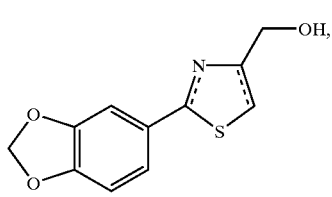

(12)

wherein ==== is defined as previously described, which is then reacted with aryl(or heteroaryl)(lower)alkyl halide or aryl(or heteroaryl)(lower)-alkylmethylsulfonyloxy to produce a compound represented by the following formula (1f):

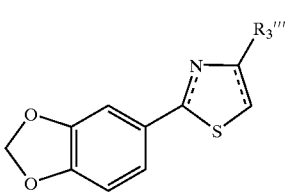

(1f)

wherein R₃‴ represents lower alkyl substituted by aryl(lower)alkoxy or 5- or 6-membered heteroaryl(lower)alkoxy containing nitrogen as the hetero atom (see, Reaction Scheme 8); or (h) 3′,4′-methylenedioxyacetophenone is reacted with bromine to produce a compound represented by the following formula (13):

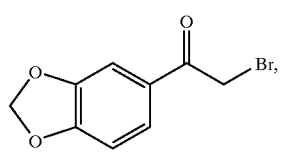

(13)

which is then reacted with thiolacetic acid to produce a compound represented by the following formula (1g):

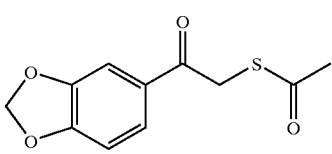

(1g)

(see, Reaction Scheme 9).

The above processes (a) to (h) will be explained more specifically below together with the Reaction Schemes.

Reaction Scheme 1

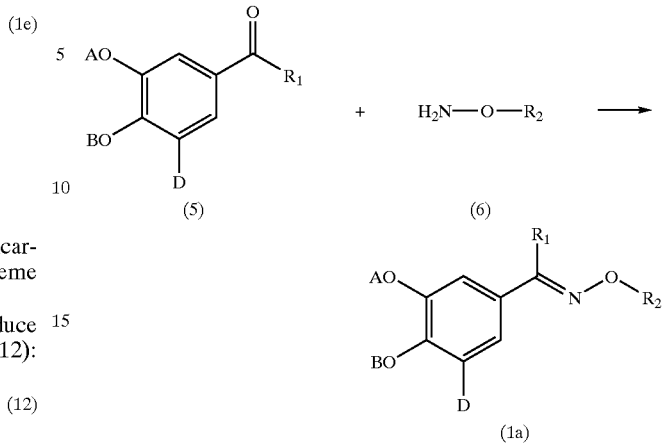

The compound of formula (5) used as a starting material in the process variant (a) according to Reaction Scheme 1 above is disclosed in Indian J. Chem., 6(6), 337–8, 1968, and can be prepared according to the procedure described therein. Any inert solvent which does not adversely affect to the reaction, preferably one or more selected from a group consisting of water, methanol, ethanol and isopropyl alcohol, particularly preferably a solvent mixture of methanol and water(10:1, v/v) can be used in process (a). In addition, inorganic bases including sodium hydroxide, potassium hydroxide, etc., or organic bases including triethylamine, etc. can be used as a reaction aid. This reaction is carried out for 2 to 5 hours at room temperature.

Reaction Scheme 2

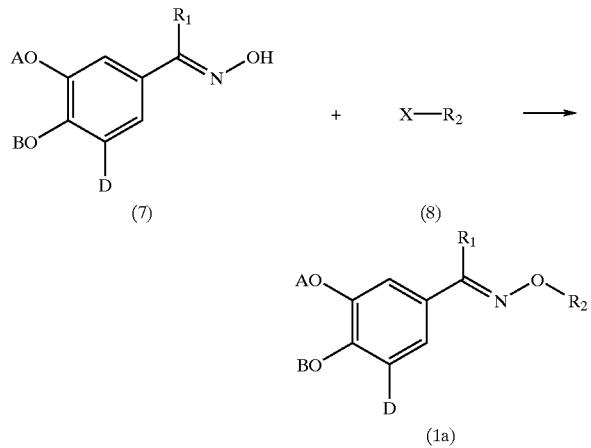

The compound of formula (7) used as a starting material in the process variant (b) according to Reaction Scheme 2 above may be prepared by oxidizing the corresponding hydroxyimino compound in the presence of sodium hydride. As examples of the reactive leaving group in the compound of formula (8), methanesulfonyloxy group can be mentioned. For example, the hydroxy group of 2-pyridylmethanol may be reacted with methanesulfonylchloride in a solvent such as methylene chloride, chloroform, etc. in the presence of a base such as triethylamine, diisopropylethylamine, etc. at −10 to 0° C. to produce the compound of formula (8) wherein X is methanesulfonyloxy and R₂ is 2-pyridylmethyl.

Reaction Scheme 3

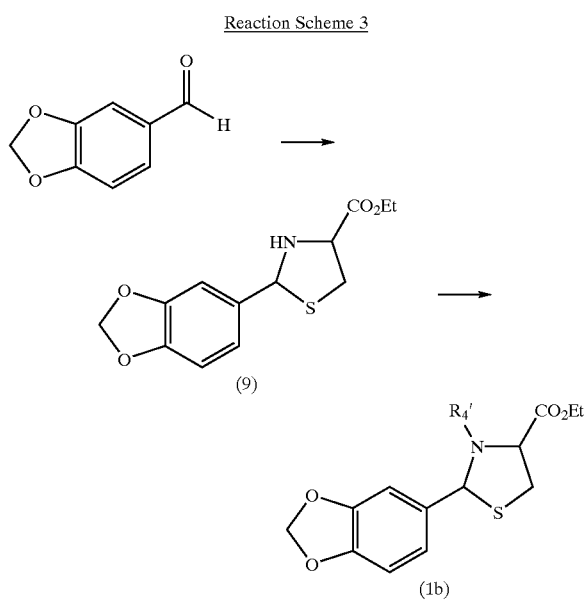

In the process variant (c) according to Reaction Scheme 3 above, piperonal is first reacted with L-cysteine ethylester hydrochloride in the presence of pyridine using a nonpolar solvent such as benzene, toluene, xylene, etc. under room temperature to warming to produce the compound of formula (9) which corresponds to the compound of formula (1) wherein $R_3$ on the thiazolidine ring is ethoxycarbonyl. Subsequently, the compound of formula (9) thus obtained is reacted with lower alkanoyl halide or anhydride which is optionally substituted by halogen, such as for example, acetyl chloride, acetic anhydride or chloroacetyl chloride in the presence of an organic base such as pyridine or triethylamine and catalytic amount of dimethylaminopyridine to produce the compound of formula (1b) wherein $R_4'$ is lower alkanoyl optionally substituted by halogen.

Reaction Scheme 4

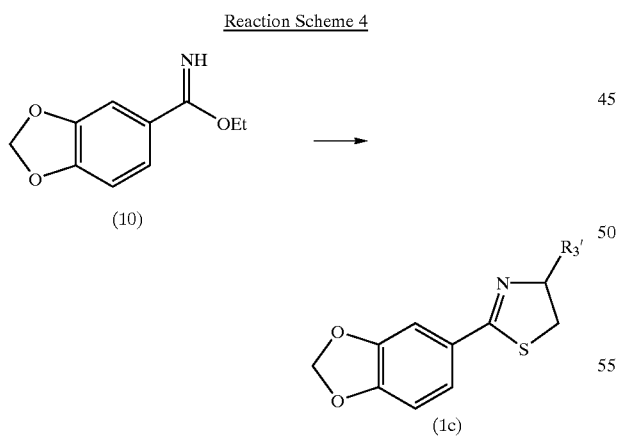

The ethylimidate compound used as a starting material in the process variant (d) according to Reaction Scheme 4 above may be prepared from piperonal. That is, the aldehyde group of piperonal is converted to hydroxyimino group according to the same procedure as Reaction Scheme 1, then the compound thus obtained is reacted with p-toluenesulfonylchloride or methanesulfonylchloride in a solvent such as methylene chloride or chloroform in the presence of an organic base such as triethylamine or diisopropylethylamine at 0° C. to room temperature in order to convert the hydroxyimino group to a nitrile group. Then, the nitrile group of the resulting compound is converted to an ethylimidate group by reacting it with ethanol saturated with hydrochloric acid gas for 5 hours to one day at 0° C. to room temperature. This procedure can be specifically depicted as the following

Reaction Scheme 5

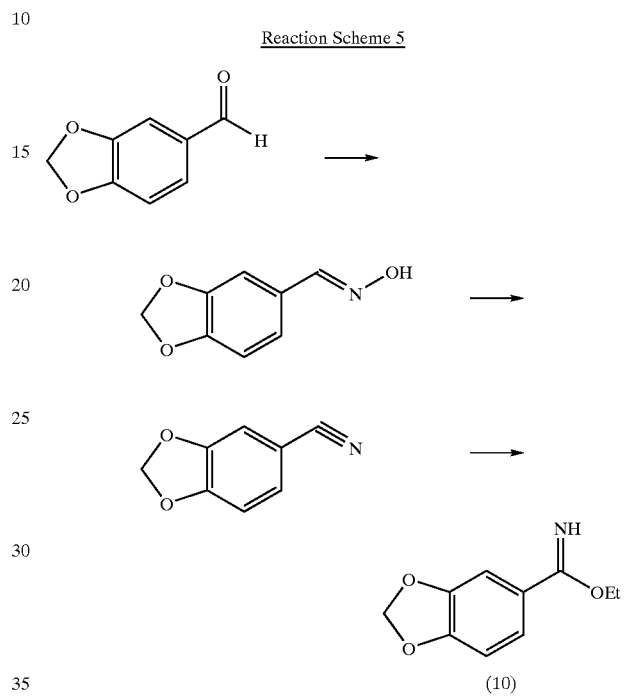

Reaction Scheme 6

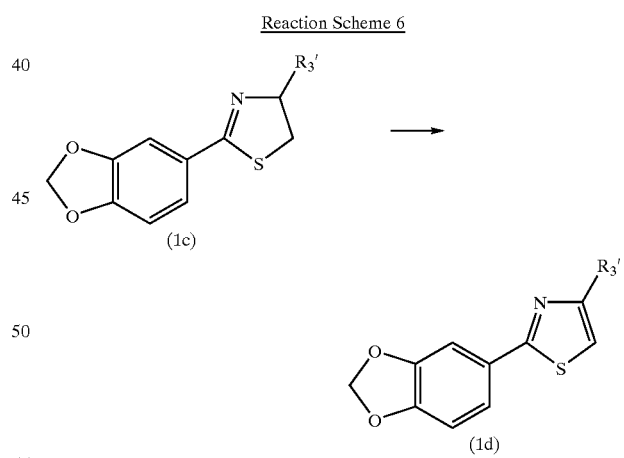

In the process variant (e) according to Reaction Scheme 6 above, the thiazoline ring of the compound of formula (1c) prepared in the above process variant (d) is oxidized to a thiazole ring in the presence of an oxidant in a nonpolar solvent such as benzene, toluene, xylene, etc., or in a solvent such as methylene chloride or carbon tetrachloride for 5 hours to one day under heating in order to produce the compound of formula (1d). As the oxidant for this reaction, manganese oxide or 2,3-dichloro-5,6-dicyano-1,4-benzoquinone, preferably manganese oxide can be used.

Reaction Scheme 7

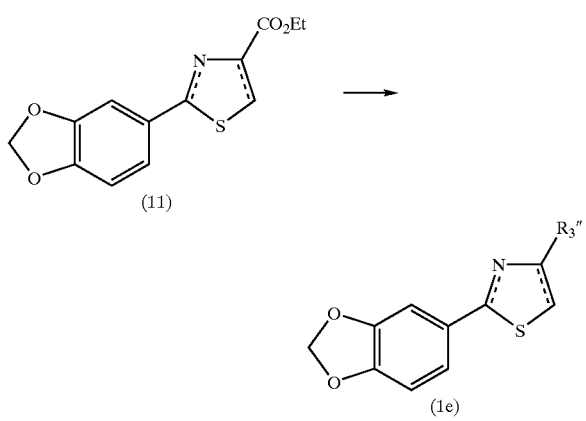

In the process variant (f) according to Reaction Scheme 7 above, the compound prepared in the process variant (d) or (e) wherein $R_3'$ is ethoxycarbonyl is used as the starting material. The starting compound is reacted with lithium hydroxide, sodium hydroxide, lower alkylamine or lower alkenylamine to produce the compound of formula (1e) wherein $R_3''$ is hydroxycarbonyl, lower alkylcarbamoyl or lower alkenylcarbamoyl.

Reaction Scheme 8

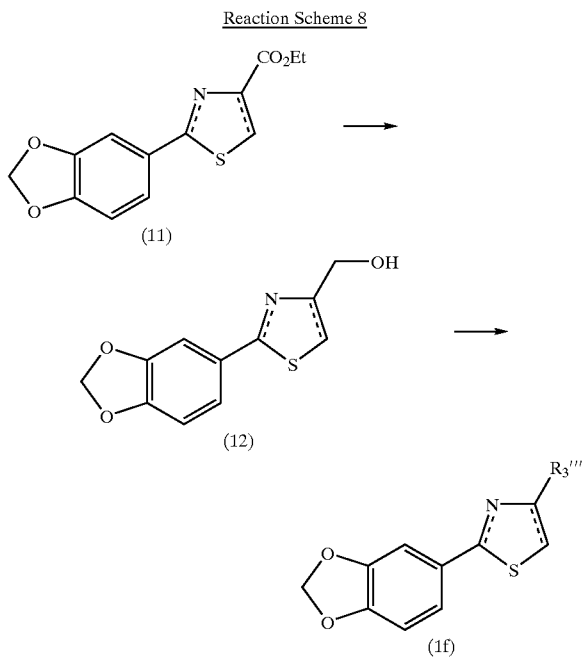

In the process variant (g) according to Reaction Scheme 8 above, the compound prepared in the process variant (d) or (e) wherein $R_3'$ is ethoxycarbonyl is first reduced by using borane-methylsulfide complex(BMS complex) or sodium bis(2-methoxyethoxy)aluminumhydride for several hours under room temperature to warming to produce the compound of formula (12). The compound of formula (12) thus obtained is then reacted with aryl(or heteroaryl)(lower)alkyl halide or aryl(or heteroaryl)(lower)alkylmethylsulfonyloxy, for example, benzyl bromide or (2-pyridyl)methyl (methylsulfonyl)oxy in the presence of a base such as sodium hydride or potassium t-butoxide in a solvent such as tetrahydrofuran or dimethylformamide to produce the compound of formula (1f) wherein $R_3'''$ is lower alkyl substituted by aryl(lower)alkoxy or 5- or 6-membered heteroaryl(lower) alkoxy containing nitrogen as the hetero atom.

Reaction Scheme 9

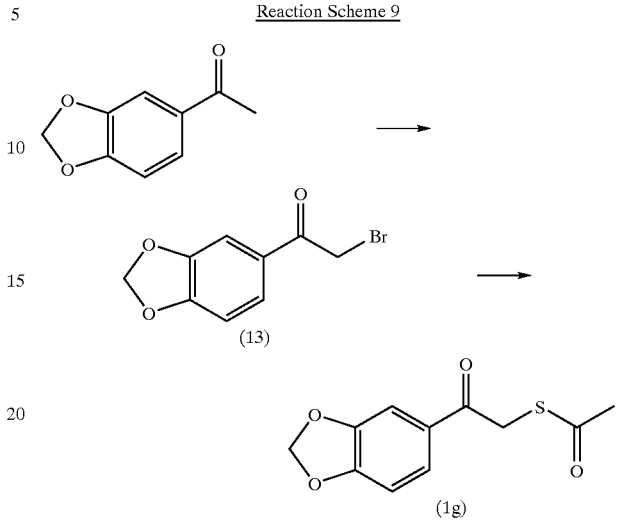

In the process variant (h) according to Reaction Scheme 9 above, 3',4'-methylenedioxyacetophenone is reacted with bromine using a solvent such as carbon disulfide, chloroform, carbon tetrachloride to produce the 2-bromo compound of formula (13) which is then reacted with thiolacetic acid in the presence of a base such as triethylamine, pyridine or diisopropylethylamine under 0° C. to slight warming to produce the desired 1-benzo[3,4-d] 1,3-dioxolan-5-yl-2-acetylthioethan-1-one of formula (1g).

The compound of formula (1) of the present invention can be prepared by processes described above or by processes appropriately combined therefrom. Those processes will be more specifically explained in the following examples.

The hepatoprotective and therapeutic effects of the compound of formula(1) on liver diseases according to the present invention were determined through carbon tetrachloride model, D-galactosamine model, thioacetamide model and D-galactosamine/lipopolysaccharide model.

The carbon tetrachloride model(see, Philippe letteron et al., Biochemical Pharmacology, 39, 12, 2027–2034, 1990; Tips, 10, 1989; Kyoichi Kagawa et al., Japan J. Pharmacol., 42, 19–26, 1986; K. T. Liu and P. Lesca, Chem. Biol. Interactions, 41, 39–47, 1982; Richard O. et al., J. Biological Chemistry, 236, 2, 1961) is used most generally. This model has been established based on the internal phenomena that carbon tetrachloride is converted by cytochrome P-450 to a toxic free radical trichloromethyl($CCl_3 \cdot$), this radical is strongly bound to a thiol group of membrane protein on microsome of liver to form a lipid radical, which is then converted to a peroxy radical in the presence of oxygen to facilitate the peroxidation reaction of membrane lipid. That is, carbon tetrachloride suppresses protein biosynthesis in the liver, induces the increase of ALT and AST values in blood, and further causes histologically the centrilobular necrosis of the liver.

The hepatoprotective effect of the compound of formula (1) was also identified by D-galactosamine model(see, Koji Hase et al., Biol. Pharm. Bull., 20, 4, 381–385, 1997; Jun-ichi Nagakawa et al., J. Pharmacology and Experimental Therapeutics, 264, 1, 1992; Toxicology of the Liver, Raven Press, New York, 1985). The N-acyl galactosamine resulted from the excess administration of D-galactosamine acts as a substrate for UDP-galactosamine or UDP-N-acyl galactosamine. But, the inordinate synthesis of UDP-glucose and UDP-hexosamine may inhibit the binding of UTP in the liver cells and biosynthsis of UDP-glucose and UDP-galactose, which finally causes the structural and functional changes of the liver cell membranes. Consequently, it results in sporadic necrosis and the increase of ALT and AST values in blood. Since the toxicity caused by D-galactosamine looks similar to the symptoms of viral hepatitis, D-galactosamine model is also used conventionally as a model for viral hepatitis.

The hepatoprotective effect of the compound of formula (1) was also identified by thioacetamide model(see, Masuda Yasusuke and Nakayama Nobue, Biochemical Pharmacology, 31, 17, 2713–2725, 1982; Liu Jie et al., Acta Pharmacologica Sinica, 16, 2, 97–102, 1995; Story D. L. et al., J. Tox. Environ. Health, 11, 483–501, 1983; Gomez-Lechon M. J. et al., Xenobiotica, 18, 6, 725–735, 1988) which is frequently used as an experimental model for liver injuries. This model has been established based on the phenomena that thioacetamide activated by P-450 S-oxidation inordinately increases the influx of calcium ion($Ca^{++}$) into the liver cells, which in turn activates calcium ion-dependent phospholipase, protease and endonuclease, changes the cell frame through the calcium ion, exhausts ATP, and consequently destroys the liver cells. Thioacetamide also damages ureogenesis pathway in liver, and the metabolite of thioacetamide inhibits the transfer of RNA and makes the liver cell membranes unstable. A series of these activities results in the destruction of the liver cells, which in turn causes the increase of ALT and AST values in blood and also causes histologically the centrilobular necrosis.

Further, the D-galactosamine/lipopolysaccharide model (see, Chris Galanos et al., Proc. Natl. Acad. Sci. USA, 76, 11, 5939–5943, 1979; Koji Hase et al., Biol. Pharm. Bull., 20, 4, 381–385, 1997; Junichi Nagakawa et al., The Journal of Pharmacology and Experimental Therapeutics, 264, 1, 1992; Nolan J. D., Hepatology, 1, 458–465, 1981; Wendel A., Methods Enzymol., 186, 675–680, 1990) which is also used in the present invention for the identification of hepatoprotective effect is based on the phenomena that liver injuries are caused by immune responses in mouse. It has been reported that such kind of liver injuries are caused not by direct tissue lesions due to the chemicals but by secretion of tumor necrosis factor(TNF)-$\alpha$, reactive oxygen, etc.(see, Hishinuma I. et al., Hepatology, 12, 1187–1191, 1990, Hase K. et al., Phytother. Res., 10, 387–392, 1996). Here, D-galactosamine supresses protein biosynthesis and as well highly increases the sensitivity of the liver cells for lipopolysaccharide by reducing uridine nucleotide. That is, when a low dose of lipopolysaccharide which does not cause any toxicities by unitary administration is administered to a mouse together with D-galactosamine, amplification of toxicity for liver injuries may occur through an immunological pathway due to the secretions of TNF-$\alpha$ and reactive oxygen from macrophage in the liver, which in turn causes the increase of ALT and AST values in blood due to the loss of function and necrosis of the liver cells.

In the present invention, the compound of formula (1) was orally administered to rats and mice as experimental animals for once, and then the protective activity of the compound against liver injuries caused by carbon tetrachloride, D-galactosamine, thioacetamide or D-galactosamine/lipopolysaccharide was measured.

The degree of liver damage in the experimental animals was determined by measuring ALT and AST values in blood(see, Biol. Pharm. Bull., 20, 4, 381–385, 1997; Toxicology and Applied Pharmacology, 95, 1–11, 1988), and the hepatoprotective activity was calculated based on the following formula(see, Planta Medica, 55, 127–132, 1989). At this time, the hepatoprotective activity can also be calculated based on the same formula by replacing ALT value with AST value.

$$\left[1 - \frac{\text{ALT value of the compound-treated group} - \text{ALT value of the normal group}}{\text{ALT value of the control group} - \text{ALT value of the normal group}}\right] \times 100,$$

in the above formula
 the normal group means a group to which only a solvent is administered,
 the control group means a group to which carbon tetrachloride, D-galactosamine, thioacetamide or D-galactosamine/lipopolysaccharide is administered, and thus the liver cells of the experimental animals are impaired, and
 the compound-treated group means a group to which the compound of formula (1) according to the present invention is orally administered for once, and then one hour after the hepatotoxic material(carbon tetrachloride, D-galactosamine, thioacetamide or D-galactosamine/lipopolysaccharide) is administered.

The experimental results show that the compound of formula (1) of the present invention exhibits a superior hepatoprotective effect to silymarin or DDB well known as a hepatoprotective agent. Further, the present inventors have performed the acute toxicity test for the compound of formula (1) according to the present invention using mouse as the test animal, and therefrom it has been identified that the compound of the present invention is considerably safe since $LD_{50}$ of the compound is more than 2,000 mg/kg when it is orally administered for once. Therefore, it is concluded that the compound of formula (1) according to the present invention is safe and also has an excellent hepatoprotective and therapeutic activity for liver diseases.

When the pharmaceutical composition according to the present invention is used for clinical purpose, it may be formulated into solid, semi-solid or liquid pharmaceutical preparations for oral or parenteral administration by combining the compound of formula (1) with a pharmaceutically acceptable inert carrier.

The pharmaceutically acceptable inert carrier which can be used for this purpose may be solid or liquid. It may be one or more selected from a group consisting of diluents, flavouring agents, solubilizing agents, lubricants, suspending agents, binders, swelling agents, etc. Specific example of the solid or liquid carrier which may be suitably used in the present invention includes lactose, starch, mannitol, cottonseed oil, etc.

When the active compound of formula (1) of the present invention is used as a medicine for prevention and treatment of liver diseases, it is preferably administered in a dose of 0.01 to 10 mg per kg of body weight per day at the first stage. However, the administration dosage can be varied with the requirement of the subject patient, severity of the liver diseases to be treated, the selected compound and the like. The prefered dosage suitable for a certain condition can be determined by a person skilled in this art according to a conventional manner. In general, the treatment is started from the amount less than the optimal dosage of the active compound and then the administration dosage increases

EXAMPLE 1

Synthesis of 1-aza-2-benzo[3,4-d]1,3-dioxolan-5-yl-1-(t-butoxy)ethene (Compound 6)

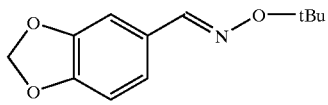

Piperonal(0.60 g, 4.00 mmol) was dissolved in methanol/water(11 ml, 10/1, v/v), and O-(t-butyl)hydroxylamine hydrochloride(0.55 g, 4.40 mmol) was added thereto. The mixture was stirred for one hour at room temperature, water was added, and then methanol was removed under reduced pressure. The residue was extracted with methylene chloride, washed with saturated sodium bicarbonate solution and saturated saline solution, dried over anhydrous magnesium sulfate, filtered and concentrated. The residue was subjected to silica gel column chromatography(eluent: ethyl acetate/n-hexane=1/3, v/v) to give the title compound(Yield 91%) as a colorless oil.

$^1$H NMR (300 MHz, CDCl$_3$): δ 1.37(s, 9H), 1.98(s, 2H), 6.78(d, 1H, J =8.0 Hz), 6.92(dd, 1H, J=1.5, 8.0 Hz), 7.22(d, 1H, J=1.5 Hz), 7.95(s, 1H)

$^{13}$C NMR(75 MHz, CDCl$_3$): δ 149.1, 148.5, 147.1, 128.1, 108.6, 105.0, 101.6, 79.3, 28.0

MASS: 465[2M+Na]$^+$,245[M+Na]$^+$,222[M+1]

EXAMPLE 2

Synthesis of 1-aza-2-benzo[3,4-d]1,3-dioxolan-5-yl-1-(benzyloxy)ethene (Compound 7)

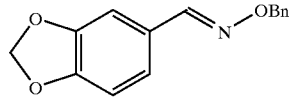

Piperonal(0.60 g, 4.00 mmol) and benzyloxyamine hydrochloride (0.70 g, 4.40 mmol) were reacted according to the same procedure as Example 1 to give the title compound (Yield 95%) as a white solid.

$^1$H NMR (300 MHz, CDCl$_3$): δ 5.16(s, 1H), 5.97(s, 1H), 6.77(d, 1H, J=8.0 Hz), 6.93(dd, 1H, J=1.5, 8.0 Hz), 7.36(m, 1H), 8.20(s, 1H)

$^{13}$C NMR (75 MHz, CDCl$_3$): δ 149.6, 149.0, 148.6, 138.0, 128.82, 128.80, 128.3, 127.0, 123.3, 108.6, 106.2, 101.8, 76.7

MASS: 256[M+1]$^+$

EXAMPLE 3

Synthesis of 1-aza-2-benzo[3,4-d]1,3-dioxolan-5-yl-vinyloxy-acetic acid(Compound 8)

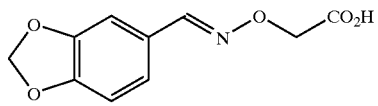

Piperonal(0.70 g, 4.66 mmol) and carboxymethoxylamine hydrochloride(0.56 g, 5.13 mmol) were reacted according to the same procedure as Example 1 to give the title compound (Yield 93%) as a white solid.

$^1$H NMR (300 MHz, DMSO-d$_6$): δ 4.80(s, 2H), 6.24(s, 2H), 7.14(d, 1H, J=8.0 Hz), 7.28(dd, 1H, J=1.5, 8.0 Hz), 7.30(d, 1H, J=8.0 Hz), 8.40(s, 1H)

$^{13}$C NMR(75 MHz, DMSO-d$_6$): δ 176.8, 154.9, 154.6, 153.4, 131.4, 128.6, 114.1, 111.0, 107.1, 76.1

EXAMPLE 4

Synthesis of 1-[(2-pyridyl)methoxy]-1-aza-2-benzo[3,4-d]1,3-dioxolan-5-ylethene(Compound 9)

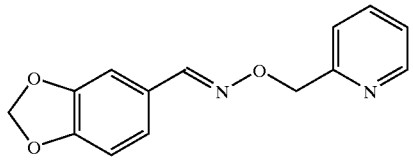

Step 1)

(2-Pyridyl)methanol(10.0 g, 91.6 mmol) was dissolved in methylene chloride(50 ml), triethylamine(15 ml, 110 mmol) was added thereto, and the mixture was cooled down to −78° C. Methanesulfonyl chloride(8.50 ml, 110 mmol) was added dropwise thereto. The resulting mixture was stirred for 30minutes at the same temperature and water(20 ml) was added to stop the reaction. The reaction mixture was extracted with methylene chloride(100 ml ×3), washed with saturated sodium bicarbonate solution and saturated saline solution, dried over anhydrous magnesium sulfate, filtered and concentrated. The residue was subjected to silica gel column chromatography(eluent: ethyl acetate/methylene chloride=1/2, v/v) to give (2-pyridyl)methyl (methylsulfonyl)oxy(17.0 g, Yield 99%) as a red oil.

$^1$H NMR (300 MHz, CDCl$_3$): δ 3.09(s, 3H), 5.33(s, 2H), 7.31(m, 1H), 7.48(d, 1H, J=7.8 Hz), 7.77(dt, 1H, J=1.7, 7.8 Hz), 8.61(m, 1H)

Step 2)

Sodium hydride(160 mg, 6.67 mmol) was dissolved in a solvent mixture of tetrahydrofuran and dimethylformamide (4:1, 15 ml), (hydroxyamino)benzo[3,4-d]1,3-dioxolan-5-ylmethane(1.0 g, 6.06 mmol) was added thereto at 0° C., and then the whole mixture was stirred for 10minutes. After (2-Pyridyl)methyl(methylsulfonyl)oxy(1.25 g, 6.67 mmol) prepared in Step 1 was added at the same temperature, the mixture was warmed to room temperature and stirred for 3 hours. The reaction mixture was concentrated and methylene chloride(300 ml) was added to the residue. The resulting mixture was washed with saturated saline solution, dried over anhydrous magnesium sulfate, filtered and concentrated. The residue was subjected to silica gel column chromatography(eluent: n-hexane/ethyl acetate=3/1, v/v) to give the title compound(1.10 g, Yield 71.1%) as a white solid.

¹H NMR (300 MHz, DMSO-d₆): δ 5.21(s, 2H), 6.07(s, 2H), 6.95(d, 1H, J=8.0 Hz), 7.10(dd, 1H, J=1.5, 8.0 Hz), 7.14(d, 1H, J=1.5 Hz), 7.32(m, 1H), 7.43(d, 1H, J=7.8 Hz), 7.81(m, 1H), 8.30(s, 1H), 8.56(m, 1H)

¹³C NMR(75 MHz, DMSO-d₆): δ 158.0, 149.7, 149.4, 148.2, 137.1, 126.2, 123.3, 123.1, 122.3, 108.9, 105.7, 101.9, 76.6

| EA: | Calculated: | C: 65.63% | H: 4.69% | N: 10.94% |
|---|---|---|---|---|
| | Experimental: | C: 65.31% | H: 4.74% | N: 10.97% |
| MASS: [M + H]⁺ 257 | | | | |

EXAMPLE 5

Synthesis of 1-aza-2-benzo[3,4-d]1,3-dioxolan-5-yl-1–1-[2-(5-methyl-2,4-thiazolyl)ethoxy]ethene (Compound 10)

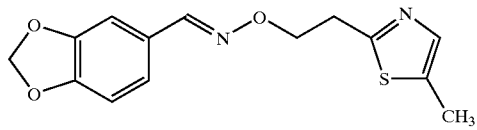

Methylsulfonyl-2-(5-methyl-2,4-thiazolyl)ethyloxy(2.41 g, 10.9 mmol) and hydroxyiminobenzo[3,4-d]1,3-dioxolan-5-ylmethane(1.50 g, 9.08 mmol) were reacted according to the same procedure as Example 4 to give the title compound (Yield 42%).

¹H NMR (300 MHz, DMSO-d₆): δ 2.32(s, 3H), 3.15(t, 2H, J=6.2 Hz), 4.24 (t, 2H, J=6.2 Hz), 6.05(s, 2H), 6.93(d, 1H, J=8.0 Hz), 7.10(dd, 1H, J=1.5, 8.0 Hz), 7.18(d, 1H, J=1.5 Hz), 8.17(s, 1H), 8.82(s, 1H)

¹³C NMR (75 MHz, DMSO-d₆): δ 150.9, 149.4, 149.3, 149.1, 148.2, 128.0, 126.4, 123.2, 108.8, 105.6, 101.8, 73.7, 26.0, 15.1

| EA: | Calculated: | C: 59.93% | H: 4.83% | N: 9.66% | S:11.03% |
|---|---|---|---|---|---|
| | Experimental: | C: 57.82% | H: 4.90% | N: 9.71% | S:11.27% |
| MASS: 290[M + H]⁺ | | | | | |

Preparation 1

Synthesis of 7-methoxybenzo [d]1,3-dioxolane-5-carboaldehyde

Step 1)

Galic acid(60 g, 353 mmol) was dissolved in methanol (600 ml), conc. sulfuric acid(18 ml) was added thereto, and the mixture was stirred under reflux for 1.5 hour. The reaction vessel was cooled down to room temperature and the reaction mixture was neutralized with saturated sodium bicarbonate solution at 0–5° C. Then, the organic solvent was removed under reduced pressure. The concentrated residue was dissolved in ethyl acetate, washed with saturated sodium bicarbonate solution and saturated saline solution, dried over anhydrous magnesium sulfate and concentrated to give methyl 3,4,5-trihydroxybenzoate(63 g, Yield 97%) as an ivory solid. This compound was used in the next step reaction without further purification.

Step 2)

Methyl 3,4,5-trihydroxybenzoate(50.0 g, 270 mmol) prepared in Step 1 and borax(54.0 g, 140 mmol) were dissoved in distilled water(1) and the mixture was stirred for 1 hour. To this solution was added sodium hydroxide(13 g, 330 mmol) dissoved in distilled water(100 ml), and the resulting mixture was stirred for 10 minutes. Dimethylsulfate(135 ml, 370 mmol) was added and the mixture was stirred again for 15 hours. The reaction solution was neutralized to pH 7–8 using conc. sulfuric acid, extracted with ethyl acetate and then subjected to silica gel column chromatography(eluent: ethyl acetate/n-hexane, 1/2, v/v) to give methyl 3,4-dihydroxy-5-methoxybenzoate(42.5 g, Yield 79%) as a white solid.

¹H NMR (300 MHz, CDCl₃): δ 3.81(s, 3H), 3.85(s, 3H), 5.70(bs, 2H), 7.15(d, 1H, J=1.7 Hz), 7.31(d, 1H, J=1.7 Hz)

Step 3)

Methyl 3,4-dihydroxy-5-methoxybenzoate(48 g, 240 mmol) prepared in Step 2 was dissolved in dimethylformamide(1.2 l), potassium fluoride (42 g, 720 mmol) and dibromomethane(42.0 g, 480 mmol) were added thereto, and the mixture was heated while stirring for 8 hours at 80° C. The reaction solution was cooled down to room temperature and the excess solvent was removed. The residue was extracted with ethyl acetate. The extract was dried over anhydrous magnesium sulfate, concentrated and then subjected to silica gel column chromatography (eluent: ethyl acetate/n-hexane=1/3, v/v) to give methyl 7-methoxybenzo[3,4-d]1,3-dioxolan-5-carboxylate(30 g, Yield 59%) as a white solid.

¹H NMR (300 MHz, CDCl₃): δ 3.91(s, 3H), 3.96(s, 3H), 6.08(s, 2H), 7.24(d, 1H, J=1.4 Hz), 7.36(d, 1H, J=1.4 Hz)

Step 4)

Methyl 7-methoxybenzo[3,4-d]1,3-dioxolane-5-carboxylate(10 g, 47.57 mmol) prepared in Step 3 was dissolved in tetrahydrofuran(200 ml), borane methylsulfide (BMS, 10M) (9.5 ml, 95.0 mmol) was added thereto, and the mixture was stirred under reflux for 1.5 hour. The reaction vessel was cooled down to room temperature and the reaction mixture was neutralized to pH 6–7 using 1N—HCl at 0–5° C., which was then extracted with ethyl acetate. The extract was washed with saturated saline solution, dried over anhydrous magnesium sulfate and concentrated. The residue was subjected to silica gel column chromatography (eluent: ethyl acetate/n-hexane=1/2, v/v) to give (7-methoxybenzo[3,4-d]1,3-dioxolan-5-yl)methan-1-ol(7.63 g, Yield 88%) as a white solid.

¹H NMR (300 MHz, CDCl₃): δ 1.88(bs, 1H), 3.83(s, 3H), 4.49(s, 2H), 5.89(s, 2H), 6.46(s, 1H), 6.47(s, 1H)

Step 5)

(7-Methoxybenzo[3,4-d]1,3-dioxolan-5-yl)methan-1-ol prepared in Step 4(7.0 g, 38.42 mmol) was dissolved in dichloromethane(150 ml), pyridiniumchlorochromate(16.6 g, 76.84 mmol) was added thereto, and the mixture was stirred for 1 hour at room temperature. The reaction mixture was filtered through cellite, filtered under reduced pressure and the filtrate was concentrated. The residue was subjected to silica gel column chromatography(eluent: ethyl acetate/n-hexane=1/3, v/v) to give the title compound(5.68 g, Yield 82%) as a white solid.

¹H NMR (300 MHz, CDCl₃): δ 3.90(s, 3H), 6.03(s, 2H), 7.00(d, 1H, J=1.4 Hz), 7.05(d, 1H, J=1.4 Hz), 9.75(s, 1H)

EXAMPLE 6

Synthesis of (hydroxyimino)(7-methoxybenzo[3,4-d]1,3-dioxolan-5-yl)-methane(Compound 11)

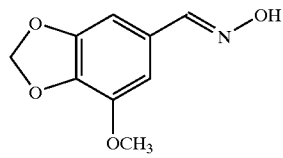

The compound prepared in Preparation 1(1 g, 5.55 mmol) and hydroxylamine hydrochloride(776 mg, 11.1 mmol) were reacted according to the same procedure as Example 1 to give the title compound(960 mg, Yield 89%) as a white solid.

$^1$H NMR (300 MHz, CDCl$_3$): δ 3.95(s, 3H), 6.01(s, 2H), 6.80(d, 1H, J=1.3 Hz), 6.82(d, 1H, J=1.2 Hz), 7.30(s, 1H), 8.02(s, 1H)

$^{13}$C NMR (CDCl$_3$+CD$_3$OD): δ 153.5, 148.0, 140.9, 131.7, 111.6, 106.0, 104.9, 60.8

MASS: [M+H]$^+$ 196, [M+Na]$^+$ 218

EXAMPLE 7

Synthesis of 6-(2-aza-2-methoxyvinyl)-4-methoxybenzo[d]1,3-dioxolane (Compound 12)

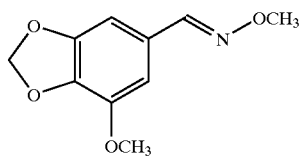

7-Methoxybenzo[d]1,3-dioxolane-5-carboaldehyde(700 mg, 3.89 mmol) prepared in Preparation 1 and methoxylamine hydrochloride(649 mg, 7.77 mmol) were reacted according to the same procedure as Example 1 to give the title compound(750 mg, Yield 92%) as a white solid.

$^1$H NMR (300 MHz, CDCl$_3$): δ 4.08(s, 3H), 4.10(s, 3H), 6.13(s, 2H), 6.89(d, 1H, J=1.4 Hz), 6.94(d, 1H, J=1.3 Hz), 8.08(s, 1H)

MASS: [M+H]$^+$ 210, [M+Na]$^+$ 232

EXAMPLE 8

Synthesis of 6-(2-((2-pyridyl)methoxy)-2-azavinyl)-4-methoxybenzo [d]1,3-dioxolane(Compound 13)

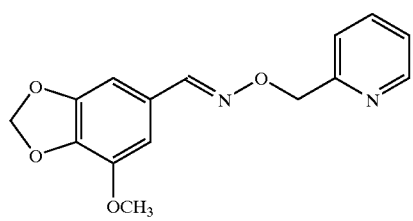

7-Methoxybenzo[d]1,3-dioxolane-5-carboaldehyde(600 mg, 3.33 mmol) prepared in Preparation 1 and ((2-pyridyl)methyl)oxyamine hydrochloride (537 mg, 3.66 mmol) were reacted according to the same procedure as Example 1 to give the title compound(800 mg, Yield 84%) as a white solid.

$^1$H NMR (300 MHz, CDCl$_3$): δ 3.95(s, 3H), 5.34(s, 2H), 6.30(s, 1H), 6.78(s, 1H), 6.82(s, 1H), 7.23(m, 1H), 7.45(d, 1H, J=7.8 Hz), 7.71(dt, 1H J=1.5, 7.8 Hz), 8.13(s, 1H), 8.62(d, 1H, J=4.5 Hz)

$^{13}$C NMR(75 MHz, CDCl$_3$): δ 158.5, 149.7, 149.5, 144.2, 137.4, 136.9, 127.0, 122.9, 122.3, 107.8, 102.2, 101.5, 77.2, 57.0

EXAMPLE 9

Synthesis of 6-(2-aza-2-(benzyloxy)vinyl)-4-methoxybenzo[d]1,3-dioxolane(Compound 14)

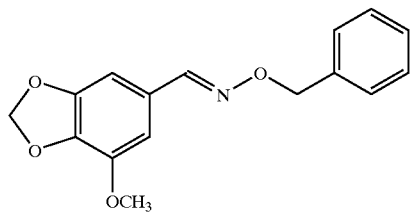

7-Methoxybenzo[d]1,3-dioxolane-5-carboaldehyde(800 mg, 4.44 mmol) prepared in Preparation 1 and benzyloxyamine hydrochloride(1.42 g, 8.88 mmol) were reacted according to the same procedure as Example 1 to give the title compound(1.05 g, Yield 83%) as a white solid.

$^1$H NMR (300 MHz, CDCl$_3$): δ 3.80(s, 3H), 5.06(s, 2H), 5.85(s, 2H), 6.62(d, 1H, J=1.4 Hz), 6.69(d, 1H, J=1.4 Hz), 7.23(m, 5H), 7.90(s, 1H)

$^{13}$C NMR (75 MHz, CDCl$_3$): δ 149.5, 149.0, 144.2, 138.0, 137.3, 128.8, 128.7, 128.4, 127.2, 107.8, 102.2, 101.4, 76.8, 57.0

MASS: [M+H]$^+$ 286, [M+Na]$^+$ 308

EXAMPLE 10

Synthesis of ethyl 4-(benzo[3,4-d]1,3-dioxolan-5-yl)-3,5-thiazolidine carboxylate(Compound 15)

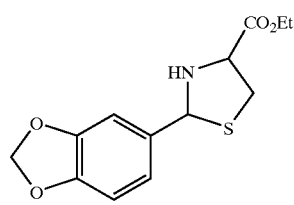

Piperonal(2.0 g, 13.32 mmol) was dissolved in 100 ml of benzene, and L-cysteine ethylester hydrochloride(3.9 g, 19.98 mmol) was added thereto. This reaction mixture was adjusted to pH 6–7 by adding pyridine(2 ml, 19.98 mmol) thereto, which was then stirred overnight. The reaction mixture was poured to 50 ml of a solvent mixture of ethyl acetate/n-hexane(1/1, v/v). The resulting solution was sequentially washed with saturated sodium bicarbonate solution and saturated saline solution. The organic layer was dried over anhydrous sodium sulfate, filtered, concentrated, and then subjected to silica gel column chromatography (eluent: ethyl acetate/n-hexane=1/3, v/v) to give the title compound(2.92 g, Yield 78%) as a pale yellow oil.

$^1$H NMR(300 MHz, CDCl$_3$): δ 1.26–1.32(2t, 4.5H, J=7.1 Hz), 2.80(dd, 1H, J=9.0, 10.0 Hz), 3.16(dd, 0.5H, J=6.0, 10.6 Hz), 3.37(dd, 0.5H, J=7.2, 10.6 Hz), 3.44(dd, 1H,

J=3.4, 10.2 Hz), 3.94(t, 1H, J=7.9 Hz), 4.16(t, 1H, J=6.4 Hz), 4.19–4.29(2q, 3H, J=7.14 Hz), 5.45(s, 1H), 5.72(s, 0.5H), 5.92(s, 0.5H), 5.95(s, 2H), 6.71–6.77(2d, 1.5H, J=7.9 Hz), 6.92–7.10 (m, 1.5H), 7.01–7.04(2s, 1.5H)/[(1R, 4R)/(1R, 4S)=2/1]

EXAMPLE 11

Synthesis of ethyl (1R,4R)-5-acetyl-4-(benzo[3,4-d]1,3-dioxolan-5-yl)-3,5-thiazolidine carboxylate (Compound 16)

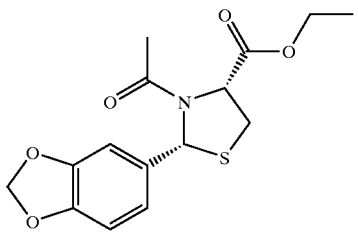

Ethyl 4-(benzo[3,4-d]1,3-dioxolan-5-yl)-3,5-thiazolidine carboxylate (5.0 g, 17.7 mmol) prepared in Example 10 was dissolved in 10 ml of a solvent mixture of pyridine/methylene chloride(1/2, v/v), and acetic anhydride(3.4 ml, 35.54 mmol) was added thereto. To the reaction solution was added a catalytic amount of dimethylaminopyridine, which was then stirred for 3 hours. The reaction mixture was sequentially washed with saturated sodium bicarbonate solution and saturated saline solution, dried over anhydrous sodium sulfate, filtered and concentrated. The residue was subjected to silica gel column chromatography(eluent: ethyl acetate/n-hexane=1/2, v/v) to give the title compound(5.46 g, Yield 95%) as a colorless oil.

$^1$H NMR(300 MHz, CDCl$_3$): δ 1.33(t, 3H, J=7.2 Hz), 1.96(s, 3H), 3.38(d, 2H, J=5.7 Hz), 4.29(q, 2H, J=7.2 Hz), 4.97(t, 2H, J=7.0 Hz), 5.90–6.03 (s&bs, 3H), 6.78(d, 1H, J=7.9 Hz), 7.12(d, 1H, J=7.9 Hz), 7.24(s, 1H)

EXAMPLE 12

Synthesis of ethyl (1R,4R)-4-(benzo[3,4-d]1,3-dioxolan-5-yl)-5-(2-chloro-acetyl)-3,5-thiazolidine carboxylate(Compound 17)

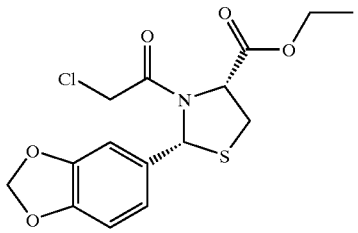

Ethyl 4-(benzo[3,4-d]1,3-dioxolan-5-yl)-3,5-thiazolidine carboxylate (5.0 g, 17.7 mmol) prepared in Example 10 was dissolved in benzene(50 ml), chloroacetylchloride(1.5 ml, 18.89 mmol) was added thereto, and the resulting mixture was stirred under reflux for 3 hours. The reaction mixture was cooled down to 0–5° C. After saturated sodium bicarbonate solution was added, the mixture was extracted with ethyl acetate(50 ml). The organic layer was washed with saturated saline solution, dried over anhydrous sodium sulfate, filtered and concentrated. The residue was subjected to silica gel column chromatography(eluent: ethyl acetate/n-hexane=1/2, v/v) to give the title compound(5.69 g, Yield 97%) as a pale yellow oil.

$^1$H NMR(300 MHz, CDCl$_3$): δ 1.25(t, 3H, J=7.2 Hz), 3.31(d, 2H, J=6.4 Hz), 3.74(d, 1H, J=12.8 Hz), 3.88(d, 1H, J=12.4 Hz), 4.30(q, 2H, J=7.2 Hz), 5.04(t, 1H, J=6.0 Hz), 5.97(s, 2H), 6.12(s, 1H), 6.78(d, 1H, J=7.9 Hz), 7.12(d, 1H, J=6.9 Hz)

Preparation 2

Synthesis of benzo[3,4-d]1,3-dioxolan-5-yl-ethoxymethaneimine

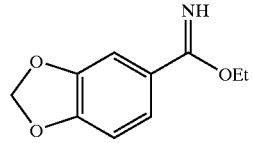

Step 1)

Piperonal(15.0 g, 0.10 mol) was dissolved in methanol (150 ml), and hydroxylamine hydrochloride(10.5 g, 0.15 mol) and water(15 ml) were added thereto. The mixture was stirred for 1 hour at room temperature, then excess water was added, and the resulting mixture was stirred for further 1 hour. The white solid thus obtained was washed with water under reduced pressure, filtered, and dried to give (hydroxyimino)-(benzo[3,4-d]1,3-dioxolan-5-yl)methane (15.7 g, Yield 95%).

$^1$H NMR(300 MHz, CDCl$_3$): δ 5.90(s, 2H), 6.70(d, 1H, J=8.0 Hz), 6.89 (d, 1H, J=8.0 Hz), 7.10(s, 1H), 8.20–8.55(bs, 1H)/5.93(s, 2H), 6.78(d, 1H, J=8.1 Hz), 6.89(d, 1H, J=8.1 Hz), 7.20(m, 1H), 7.69(s, 1H)/[E/Z=5.4/1]

Step 2)

The compound prepared in Step 1(15.7 g, 0.095 mol) was dissolved in methylene chloride(160 ml), triethylamine(32.9 ml, 0.236 mol) was added thereto, and the resulting mixture was cooled down to 0° C. Methane-sulfonylchloride(8.82 ml, 0.114 mol) was added to the reaction solution, which was then stirred for 30 minutes at the same temperature. The reaction mixture was filtered and then the filtrate was sequentially washed with 1N-hydrochloric acid solution, saturated sodium bicarbonate solution and saturated saline solution. The organic layer was dried over anhydrous magnesium sulfate and concentrated to give benzo[3,4-d]1,3-dioxolan-5-carbonitrile(13.83 g, Yield 99%) as a pale yellow solid.

$^1$H NMR(300 MHz, CDCl$_3$): δ 6.09(s, 2H), 6.88(d, 1H, J=8.1 Hz), 7.05(d, 1H, J=1.5 Hz), 7.23(dd, 1H, J=1.5, 8.1 Hz)

$^{13}$C NMR(75 MHz, CDCl$_3$): δ 151.9, 148.4, 128.6, 119.2, 111.8, 109.5, 105.4, 102.6

Step 3)

The compound prepared in Step 2(11.3 g, 76.80 mmol) was dissolved in ethanol saturated with hydrochloric acid gas(500 ml), which was then stirred for 5 hours at room temperature and concentrated. The residue was dissolved in ethyl acetate. The resulting solution was sequentially washed with saturated sodium bicarbonate solution and saturated saline solution, dried over anhydrous magnesium sulfate, filtered and concentrated. To the residue was added 50 me of a solvent mixture of n-hexane/ethyl acetate(20/1, v/v), then the resulting mixture was stirred for one day and filtered to give the title compound(13.35 g, Yield 90%) as a pale yellow solid.

¹H NMR(300 MHz, CDCl₃): δ 1.39(t, 3H, J=7.1 Hz), 4.21(q, 2H, 7.1 Hz), 5.92(s, 2H), 6.73(d, 1H, J=8.2 Hz), 7.14(d, 1H, J=1.6 Hz), 7.23(dd, 1H, J=1.6, 8.1 Hz)

EXAMPLE 13

Synthesis of ethyl (1R)-4-(benzo[3,4-d]1,3-dioxolan-5-yl)-3,5-thiazoline carboxylate (Compound 18)

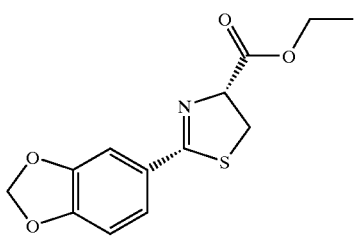

(Benzo[3,4-d]1,3-dioxolan-5-yl)-ethoxymethaneimine prepared in Preparation 2(3.0 g, 15.53 mmol) was dissolved in ethanol(100 ml), L-cysteine ethylester hydrochloride(5.76 g, 31.10 mmol) was added thereto, and the mixture was stirred for one day at room temperature. After the reaction mixture was concentrated, the residue was dissolved in ethyl acetate. This solution was washed with saturated saline solution, dried over anhydrous magnesium sulfate, filtered and concentrated. The residue was subjected to silica gel column chromatography(eluent: ethyl acetate/n-hexane=1/6, v/v) to give the title compound(2.61 g, Yield 60%) as a white solid.

¹H NMR (300 MHz, CDCl₃): δ 1.25(t, 3H, J=7.1 Hz), 3.50–3.64(m, 2H), 4.21(q, 2H, J=7.1 Hz), 5.15(t, 1H, J=9.0 Hz), 5.94(s, 2H), 6.74(d, 1H, J=8.1 Hz), 7.29(dd, 1H, J=1.7, 8.1 Hz), 7.35(d, 1H, J=1.7 Hz)

EXAMPLE 14

Synthesis of (1R)-4-(benzo[3,4-d]1,3-dioxolan-5-yl)-1-(N-methylcarbamoyl)-3,5-thiazoline (Compound 19)

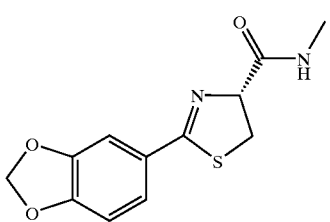

Ethyl (1R)-4-(benzo[3,4-d]1,3-dioxolan-5-yl)-3,5-thiazoline carboxyl-ate prepared in Example 13(1.3 g, 4.65 mmol) was dissolved in 40% methylamine(125 ml), and the resulting solution was stirred for one day at room temperature and filtered. By stirring the crystal thus obtained in n-hexane the purified title compound(0.69 g, Yield 56%) as a white solid was obtained.

¹H NMR (300 MHz, CDCl₃): δ 2.74(d, 3H, J=5.0 Hz), 3.48(dd, 1H, J=9.5, 11.3 Hz), 3.60(dd, 1H, J=9.6, 11.3 Hz), 4.99(t, 1H, J=9.6 Hz), 5.90 (s, 2H), 6.68(bs, 1H), 6.70(d, 1H, J=8.1 Hz), 7.22(dd, 1H, J=1.7, 8.1 Hz), 7.26(d, 1H, J=1.6 Hz)

¹³C NMR (75 MHz, CDCl₃): δ 172.4, 170.5, 151.1, 148.4, 127.4, 124.5, 108.5, 108.3, 102.2, 79.5, 36.2, 26.5

MASS: [M+H]⁺ 265

EXAMPLE 15

Synthesis of (1R)-4-(benzo[3,4-d]1,3-dioxolan-5-yl)-1-(N-allylcarbamoyl)-3,5-thiazoline(Compound 20)

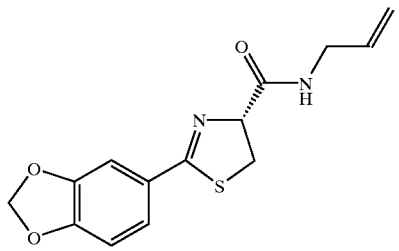

Ethyl (1R)-4-(benzo[3,4-d]1,3-dioxolan-5-yl)-3,5-thiazoline carboxylate prepared in Example 13(0.08 g, 0.29 mmol) was dissolved in methanol (1 ml), allylamine(0.04 ml, 0.57 mmol) and sodium cyanide(0.014 g, 0.029 mmol) were added thereto, and the resulting mixture was stirred for 4 hours at 50° C. and then concentrated. The residue was dissolved in ethyl acetate, washed with saturated saline solution, dried over anhydrous magnesium sulfate, filtered and concentrated. The residue was subjected to silica gel column chromatography(eluent: ethyl acetate/n-hexane=1/4, v/v) to give the title compound(0.03 g, Yield 34%) as a white solid.

¹H NMR (300 MHz, CDCl₃): δ 3.67(d, 2H, J=9.1 Hz), 3.88(dd, 2H, J=5.8, 11.6 Hz), 5.06–5.17(m, 3H), 5.73–5.84 (m, 1H), 5.98(s, 2H), 6.78(d, 1H, J=8.0 Hz), 7.03(bs, 1H), 7.19–7.37(m, 2H)

Preparation 3

Synthesis of 2-(benzo[3,4-d]1,3-dioxolan-5-yl)-1,3-thiazoline(Compound 5)

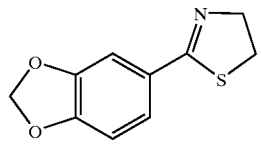

The title compound of Preparation 2(14.38 g, 74.43 mmol) was dissolved in ethanol(250 ml), and mercaptoethylamine hydrochloride(12.68 g, 111.61 mmol) was added thereto. The resulting mixture was stirred for one day at room temperature and concentrated. The residue was dissolved in ethyl acetate, sequentially washed with saturated sodium bicarbonate solution and saturated saline solution, dried over anhydrous magnesium sulfate, and concentrated. The residue was subjected to silica gel column chromatography(eluent: ethyl acetate/n-hexane=1/6, v/v) to give the title compound(13.73 g, Yield 89%) as a white solid.

¹H NMR(300 MHz, CDCl₃): δ 3.41(t, 2H, J=8.2 Hz), 4.44(t, 2H, J=8.2 Hz), 6.04(s, 2H), 6.84(d, 1H, J=8.1 Hz), 7.36(dd, 1H, J=1.7, 8.1 Hz), 7.40(d, 1H, J=1.7 Hz)

¹³C NMR(75 MHz, CDCl₃): δ 168.0, 150.5, 148.3, 128.1, 124.2, 108.5, 108.4, 102.0, 65.4, 34.2

MASS: [M+H]⁺ 208

EXAMPLE 16

Synthesis of 2-(benzo[3,4-d]1,3-dioxolan-5-yl)-1,3-thiazole(Compound 21)

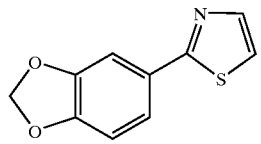

2-(Benzo[3,4-d]1,3-dioxolan-5-yl)-1,3-thiazoline prepared in Preparation 3(5.0 g, 24.12 mmol) was dissolved in benzene(250 ml), and then manganese oxide(62.92 g, 723.7 mmol) was added thereto. The resulting mixture was stirred under reflux for 3 hours, filtered through cellite, and then concentrated. The residue was subjected to silica gel column chromatography(eluent: ethyl acetate/n-hexane=1/6, v/v) to give the title compound(2.74 g, Yield 55%) as a white solid.

$^1$H NMR(300 MHz, CDCl$_3$): δ 5.94(s, 2H), 6.78(dd, 1H, J=3.2, 5.2 Hz), 7.17(d, 1H, J=3.3 Hz), 7.38–7.41(m, 2H), 7.72(d, 1H, J=3.3 Hz)

$^{13}$C NMR(75 MHz, CDCl$_3$): δ 163.2, 144.4, 143.4, 138.5, 123.3, 116.3, 113.2, 103.7, 102.0, 96.7

MASS: [M+H]$^+$ 206

EXAMPLE 17

Synthesis of ethyl 4-(benzo[3,4-d]1,3-dioxolan-5-yl)-3,5-thiazole carboxylate(Compound 22)

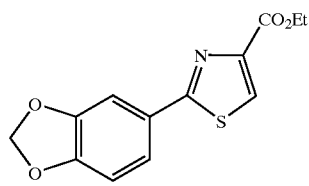

Ethyl (1R)-4-(benzo[3,4-d]1,3-dioxolan-5-yl)-3,5-thiazoline carboxylate prepared in Example 13(1.25 g, 4.47 mmol) was dissolved in methylene chloride(60 ml), and the reaction solution was cooled down to 0° C. To this solution was added manganese oxide(3.89 g, 44.76 mmol), and the resulting mixture was stirred for 6 hours and filtered through cellite. The filtrate was concentrated, and to the residue was added n-hexane. The resulting mixture was stirred and filtered to give the title compound(1.0 g, Yield 81%) as a white solid.

$^1$H NMR (300 MHz, CDCl$_3$): δ 1.45(t, 3H, J=7.1 Hz), 4.46(q, 2H, J=7.1 Hz), 6.06(s, 2H), 6.89(d, 1H, J=7.9 Hz), 7.53(dd, 1H, J=1.7, 8.0 Hz), 7.56(d, 1H, J=1.7 Hz), 8.11(s, 1H)

EXAMPLE 18

Synthesis of 4-(benzo[3,4-d]1,3-dioxolan-5-yl)-1-(N-methylcarbamoyl)-3,5-thiazole(Compound 23)

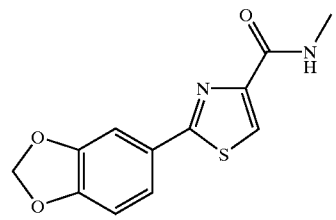

Ethyl 4-(benzo[3,4-d]1,3 -dioxolan-5-yl)-3,5 -thiazole carboxylate prepared in Example 17(1.0 g, 3.61 mmol) was dissolved in 40% methylamine(97 ml). This solution was stirred for 6 hours at room temperature, and then filtered while washed with water. The crystal thus obtained was dissolved in methylene chloride, dried over anhydrous magnesium sulfate, filtered and concentrated. To the residue was added a solvent mixture of n-hexane/ethyl acetate(10/1, v/v), and then the mixture was stirred and filtered to give the title compound(0.84 g, Yield 89%) as a white solid.

$^1$H NMR (300 MHz, CDCl$_3$): δ 3.05(d, 3H, J=8.5 Hz), 6.06(s, 2H), 6.89(d, 1H, J=8.6 Hz), 7.45(dd, 1H, J=1.8, 8.5 Hz), 7.45(bs, 1H), 7.48(d, 1H, J=1.8 Hz), 8.03(s, 1H)

$^{13}$C NMR(75 MHz, CDCl$_3$): δ 168.1, 162.2, 150.9, 150.1, 148.8, 127.7, 122.3, 121.7, 109.1, 107.1, 102.1, 26.4

MASS: [M+H]$^+$ 263

EXAMPLE 19

Synthesis of 2-(benzo[3,4-d]1,3-dioxolan-5-yl)-4-hydroxycarbonyl-1,3-thiazole(Compound 24)

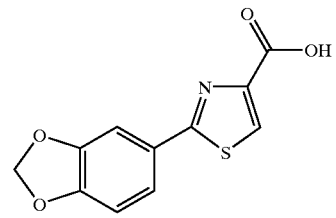

Ethyl 4-(benzo[3,4-d]1,3-dioxolan-5-yl)-3,5-thiazole carboxylate prepared in Example 17(3.2 g, 11.5 mmol) was dissolved in acetonitrile(30 ml), and sodium hydroxide(1.38 g, 34.6 mmol) was added to the reaction mixture. This reaction solution was stirred for 2 hours at room temperature and concentrated. The residue was extracted with ethyl acetate, dried over anhydrous sodium sulfate, and concentrated. The residue was recrystallized from ethyl acetate/n-hexane(1/5, v/v) to give the title compound(1.6 g, Yield 56%) as a white crystal.

$^1$H NMR(300 MHz, CD$_3$OD): δ 5.92(s, 2H), 6.78(d, 1H, J=6.5 Hz), 7.19 (s, 2H), 8.06(s, 1H)

EXAMPLE 20

Synthesis of 2-(benzo[3,4-d]1,3-dioxolan-5-yl)-4-hydroxymethyl-1,3-thiazole(Compound 25)

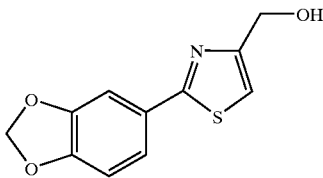

Ethyl 4-(benzo[3,4-d]1,3-dioxolan-5-yl)-3,5-thiazole carboxylate prepared in Example 17(1.93 g, 6.96 mmol) was dissolved in tetrahydrofuran(THF, 30 ml), borane-methylsulfide complex(10M in THF, 2.1 ml, 20.88 mmol) was added thereto, and the mixture was stirred under reflux for 2 hours. The reaction vessel was cooled down to 0° C., and the reaction was stopped by slowly adding 1N—HCl. The pH of the reaction solution was adjusted to 6–7 using saturated sodium bicarbonate solution, and then the organic solvent was removed under reduced pressure. The residue was extracted with ethyl acetate, and then the extract was washed with saturated saline solution, dried over anhydrous magnesium sulfate, and concentrated. The concentrate was recrystallized from ethyl acetate and n-hexane(EA/HA=1/1, v/v) to give the title compound(1.04 g, Yield 64%) as a white solid.

$^1$H NMR(300 MHz, CDCl$_3$): δ 2.46(bs, 1H), 4.79(s, 2H), 6.03(s, 2H), 6.88(dd, 1H, J=3.0, 5.6 Hz), 7.13(s, 1H), 7.48(dd, 1H, J=1.7, 5.5 Hz)

EXAMPLE 21

Synthesis of 2-(benzo [3,4-d]1,3-dioxolan-5-yl)-4-benzyloxymethyl-1,3-thiazole(Compound 26)

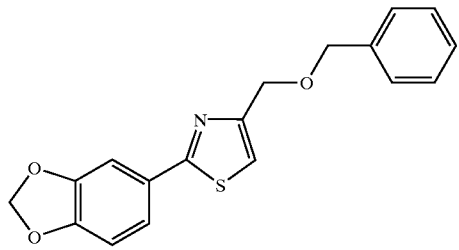

2-(Benzo[3,4-d]1,3-dioxolan-5-yl)-4-hydroxymethyl-1,3-thiazole prepared in Example 20(100 mg, 0.43 mmol) was dissolved in N,N-dimethylformamide(2 ml). Right after sodium hydride(15.4 mg, 0.64 mmol) was added to the reaction solution at 0~5° C., benzyl bromide(76 μl, 0.64 mmol) was added thereto. The resulting mixture was stirred for 1 hour while slowly warmed to room temperature. To the reaction mixture was added saturated sodium bicarbonate solution. Then the mixture was extracted with ethyl acetate/n-hexane(1/2, v/v), washed with saturated saline solution, dried over anhydrous magnesium sulfate, and concentrated. The concentrate was subjected to silica gel column chromatography(eluent: ethyl acetate/n-hexane=1/10, v/v) to give the title compound(135 mg, Yield 96%) as a white solid.

$^1$H-NMR(300 MHz, CDCl$_3$): δ 4.70(s, 2H), 4.72(s, 2H), 6.01(s, 2H), 6.87(d, 1H, J=8.6 Hz), 7.19(s, 1H), 7.39(m, 7H)

EXAMPLE 22

Synthesis of 2-(benzo[3,4-d]1,3-dioxolan-5-yl)-4-(2-pyridylmethoxymethyl)-1,3-thiazole (Compound 27)

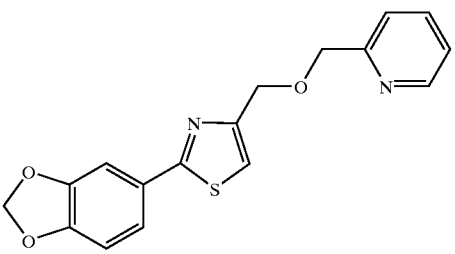

2-Pyridylcarbinol(0.19 ml, 1.71 mmol) was dissolved in methylene chloride(2 ml), triethylamine(0.59 ml, 4.27 mmol) was added thereto, and the mixture was stirred for 10 minutes at 0° C. Then, methanesulfonyl-chloride(0.26 ml, 3.41 mmol) was added and the resulting mixture was stirred for 10 minutes at the same temperature. The reaction solution was sequentially washed with saturated sodium bicarbonate solution and saturated saline solution, dried over anhydrous sodium sulfate, and concentrated to give 2-(methanesulfonyloxymethyl)pyridine(315 mg).

2-(Benzo[3,4-d]1,3-dioxolan-5-yl)-4-hydroxymethyl-1,3-thiazole prepared in Example 20(200 mg, 0.85 mmol) was dissolved in N,N-dimethylformamide(5 ml), and sodium hydride(30.7 mg, 1.28 mmol) was added thereto at 0–5° C. To this mixture was added dropwise 2-(methane sulfonyloxymethyl)pyridine(315 mg) dissolved in 1 ml of tetrahydrofuran, and the resulting mixture was stirred for 2 hours at room temperature. Saturated sodium bicarbonate solution was added to the reaction mixture, which was then extracted with a solvent mixture of ethyl acetate/n-hexane (1/1, v/v). The extract was washed with saturated saline solution, dried over anhydrous sodium sulfate, and concentrated. The concentrate was subjected to silica gel column chromatography(eluent: ethyl acetate/n-hexane=1/2, v/v) to give the title compound(180 mg, Yield 65%) as an ivory solid.

$^1$H NMR (300 MHz, CDCl$_3$): δ 4.73(s, 2H), 4.74(s, 2H), 5.93(s, 2H), 6.78 (d, 1H, J=8.6 Hz), 7.10(m, 1H), 7.13(s, 1H), 7.37(m, 2H), 7.45(d, 1H, J=7.8 Hz), 7.63(dt, 1H, J=1.7, 7.7 Hz), 8.49(d, 1H, J=4.8 Hz)

$^{13}$C NMR(75 MHz, CDCl$_3$): δ 154.8, 149.7, 149.5, 148.6, 137.0, 128.5, 122.8, 121.9, 121.5, 115.6, 108.9, 107.3, 101.9, 74.0, 69.3

EXAMPLE 23

Synthesis of 1-(benzo[3,4-d]1,3-dioxolan-5-yl)-2-acetylthioethan-1-one (Compound 28)

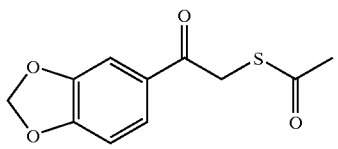

3',4'-(Methylenedioxy)-acetophenone(30 g, 0.183 mol) was dissolved in carbon disulfide(1l) under slight warming, and bromine(18.8 ml, 0.366 mol) was slowly added dropwise thereto, by which the exothermic reaction was proceeded. After all the bromine was added dropwise, the resulting mixture was stirred for 1 hour, sequentially washed with saturated sodium bisulfite solution and saturated saline solution, dried over anhydrous magnesium sulfate, and concentrated. The mixture of 1-(benzo[3,4-d]1,3-dioxolan-5-yl)-2-bromoethan-1-one thus obtained as a pale yellow solid and 1-(benzo[3,4-d]1,3-dioxolan-5-yl)-2,2-dibromoethan-1-one was dissolved in methylene chloride (600 ml), and thiolacetic acid (15.7 ml, 0.219 mol) was added thereto. To the reaction solution was added triethylamine(38.2 ml, 0.274 mol) at 0–5° C. The resulting mixture was stirred for 1 hour while warmed to room temperature. The reaction mixture was sequentially washed with 1N-hydrochloric acid solution, saturated sodium bicarbonate solution and saturated saline solution, dried over anhydrous magnesium sulfate, and concentrated. The concentrate was subjected to silica gel column chromatography (eluent: ethyl acetate/n-hexane=1/7, v/v), and recrystallized from a solvent mixture of ethyl acetate/n-hexane(1/5, v/v) to give the title compound(33.5 g, Yield 77%) as a white solid.

$^1$H NMR (300 MHz, CDCl$_3$): δ 2.42(s, 3H), 4.36(s, 2H), 6.06(s, 2H), 6.89 (d, 1H, J=8.2 Hz), 7.50(s, 1H), 7.67(dd, 1H, J=1.7, 8.1 Hz)

$^{13}$C NMR(75 MHz, CDCl$_3$): δ 192.1, 181.2, 150.2, 146.2, 128.2, 122.9, 106.1, 105.9, 99.9, 34.2, 28.0

MASS: [M+H]$^+$ 239 [M+Na]$^+$ 261

| Formulation 1: Tablet | |
| --- | --- |
| The active ingredient | 5.0 mg |
| Lactose BP | 150.0 mg |
| Starch BP | 30.0 mg |
| Pregellatinated Corn Starch BP | 15.0 mg |
| Stearic Acid Magnesium | 1.0 mg |

After the active ingredient was sieved, it was mixed with lactose, starch and pregellatinated corn starch. Suitable volume of distilled water was added thereto and the whole mixture was granulated. This granule was dried and mixed with stearic acid magnesium, which was then pressed to give a tablet.

| Formulation 2: Capsule | |
| --- | --- |
| The active ingredient | 5.0 mg |
| Starch 1500 | 100.0 mg |
| Stearic Acid Magnesium BP | 1.0 mg |

After the active ingredient was sieved, it was mixed with excipients. The whole mixture was filled into a gellatin capsule to give a capsule.

| Formulation 3: Injection | |
| --- | --- |
| The active ingredient | 100 μg/ml |
| Diluted Hydrochloric Acid BP | q.s. to pH 3.5 |
| Injectable Sodium Chloride BP | 1 ml or less |

The active ingredient was dissolved in a suitable volume of injectable sodium chloride BP. The resulting solution was adjusted to pH 3.5 with the diluted hydrochloric acid BP. Then, the volume was adjusted with the injectable sodium chloride BP, and the mixture was thoroughly mixed. The solution was filled into a transparent 5 ml volume ampoule of type 1, and the glass was sealed. Then, the contents of the ampoule was sterilized by an autoclave for more than 15 minutes at 120° C. to give an injection.

Experimental Example 1

Inhibitory Effect Against Liver Injuries Caused by Carbon Tetrachloride

The hepatoprotective effect of the compound of the present invention was identified according to a known procedure(see, Philippe letteron et al., Biochemical Pharmacology, 39, 12, 2027–2034, 1990), and the protocol may be described in brief as follows.

A. The Test Animal

Rats(SD, male, 180~200 g) and mice(ICR, male, 27–35 g) used in the test were allowed in a condition of temperature 22±1° C. and relative humidity 60±5%. Feed and water were provided with no restriction while light and darkness were changed at an interval of 12 hours.

B. Administration of Drugs

The compound of the present invention was suspended in a solvent corn oil in concentrations of 16.7, 50 mg/2 ml(rat) and 16.7, 50 mg/10 ml(mouse), respectively. This suspensions were administered in a dose of 2 ml/kg(rat) and 10 ml/kg(mouse). Each group included 8 test animals, and the test compound was orally administered once per animal. After 30 minutes(rat) or 1 hour(mouse) from the administration of the test compound, 10% carbon tetrachloride in corn oil solution was intraperitoneally injected in doses of 2 ml/kg in rats and 0.15 ml/kg in mice. As the control compounds, silymarin and DDB were selected.

C. Serum Collection and Biochemical Analysis

The test animals were provided with no feed and sufficient water for 24 hours from the administration of carbon tetrachloride. Then, the test animals were put under slight anesthesia and their abdomens were opened in order to take blood from the inferior vena cava. This blood was centrifuged to obtain sera. ALT and AST values in the sera were measured using blood chemistry analyzer(Vitalab, Selectra II, Merck). The statistical significance for the test result of each group was examined based on Student's t-test, and the result was recognized as having a statistical significance when its P value is less than 5%.

When the typical compounds are orally administered to rats and mice, the inhibitory effects thereof against liver injuries caused by carbon tetrachloride are summarized in the following Tables 2 and 3.

TABLE 2

Inhibitory Effect against Liver Injuries caused by Carbon Tetrachloride in Rats

| Compound | Dose(mg/kg) | Administration Route | Inhibitory Effect against Liver Injuries (%) ALT |
| --- | --- | --- | --- |
| Silymarin | 50 | p.o. | 29 |
| DDB | 50 | p.o. | 21 |
| Compound 1 | 1.9 | p.o. | 44 |
| | 5.6 | p.o. | 43 |
| | 16.7 | p.o. | 68 |
| | 50.0 | p.o. | 84 |
| Compound 9 | 1.9 | p.o. | 61 |
| | 5.6 | p.o. | 60 |
| | 16.7 | p.o. | 56 |
| | 50.0 | p.o. | 75 |

TABLE 2-continued

Inhibitory Effect against Liver Injuries caused by Carbon Tetrachloride in Rats

| Compound | Dose(mg/kg) | Administration Route | Inhibitory Effect against Liver Injuries (%) ALT |
|---|---|---|---|
| Compound 13 | 1.9 | p.o. | 53 |
|  | 5.6 | p.o. | 49 |
|  | 16.7 | p.o. | 59 |
|  | 50.0 | p.o. | 67 |
| Compound 21 | 16.7 | p.o. | 63 |
|  | 50.0 | p.o. | 67 |
| Compound 28 | 16.7 | p.o. | 14 |
|  | 50.0 | p.o. | 41 |

TABLE 3

Inhibitory Effect against Liver Injuries caused by Carbon Tetrachloride in Mice

| Compound | Dose(mg/kg) | Administration Route | Inhibitory Effect against Liver Injuries (%) AST | ALT |
|---|---|---|---|---|
| Silymarin | 50 | p.o. | 65 | 68 |
| DDB | 50 | p.o. | 6 | 22 |
| Compound 1 | 1.9 | p.o. | — | 50 |
|  | 5.6 | p.o. | — | 79 |
|  | 16.7 | p.o. | — | 100 |
|  | 50.0 | p.o. | — | 100 |
| Compound 9 | 1.9 | p.o. | — | 64 |
|  | 5.6 | p.o. | — | 64 |
|  | 16.7 | p.o. | — | 87 |
|  | 50.0 | p.o. | — | 98 |
| Compound 13 | 1.9 | p.o. | — | 35 |
|  | 5.6 | p.o. | — | 43 |
|  | 16.7 | p.o. | — | 69 |
|  | 50.0 | p.o. | — | 100 |
| Compound 21 | 16.7 | p.o. | 97 | 99 |
|  | 50.0 | p.o. | 100 | 100 |
| Compound 28 | 16.7 | p.o. | 94 | 93 |
|  | 50.0 | p.o. | 100 | 100 |

Experimental Example 2
Inhibitory Effect Against Liver Injuries Caused by D-galactosamine The hepatoprotective effect of the compound of the present invention was identified according to a known procedure(see, Koji Hase et al., Biol. Pharm. Bull., 20, 4, 381–385, 1997), and the protocol may be described in brief as follows.

A. The Test Animal

Rats(SD, male, 180~200 g) as the test animal were allowed in a condition of temperature 22±1° C. and relative humidity 60±5%. Feed and water were provided with no restriction while light and darkness were changed at an interval of 12 hours.

B. Administration of Drugs

The compound of the present invention was suspended in a solvent corn oil, and this suspension was administered in a dose of 2 ml/kg. Each group included 8 test animals, and the test compound was orally administered for once per animal. After 30 minutes from the administration of the test compound, D-galactosamine solution(concentration: 200 mg/ml) in physiological saline was intraperitoneally injected in a dose of 2 ml/kg. As the control compounds, silymarin and DDB were selected.

C. Serum Collection and Biochemical Analysis

The test animals were provided with no feed and sufficient water for 24 hours from the administration of D-galactosamine. Then, the test animals were put under slight anesthesia and their abdomens were opened in order to take blood from the inferior vena cava. This blood was centrifuged to obtain sera. ALT and AST values in the sera were measured using blood chemistry analyzer(Vitalab, Selectra II, Merck). The statistical significance for the test result of each group was examined based on Student's t-test, and the result was recognized as having a statistical significance when its P value is less than 5%.

When the typical compounds are orally administered to rats, the inhibitory effects thereof against liver injuries caused by D-galactosamine are summarized in the following Table 4.

TABLE 4

Inhibitory Effect against Liver Injuries caused by D-galactosamine in Rats

| Compound | Dose(mg/kg) | Administration Route | Inhibitory Effect against Liver Injuries(%) AST | ALT |
|---|---|---|---|---|
| Silymarin | 50 | p.o. | −35 | −33 |
| DDB | 50 | p.o. | 12 | 28 |
| Compound 1 | 16.7 | p.o. | — | 5 |
|  | 50.0 | p.o. | — | 12 |
| Compound 13 | 5.6 | p.o. | — | 34 |
|  | 16.7 | p.o. | — | 35 |
|  | 50.0 | p.o. | — | 67 |
| Compound 21 | 5.6 | p.o. | 29 | 27 |
|  | 16.7 | p.o. | 29 | 32 |
|  | 50.0 | p.o. | 46 | 56 |
| Compound 28 | 5.6 | p.o. | 48 | 42 |
|  | 16.7 | p.o. | 55 | 51 |
|  | 50.0 | p.o. | 55 | 52 |

Experimental Example 3
Inhibitory Effect Against Liver Injuries Caused by Thioacetamide The hepatoprotective effect of the compound of the present invention was identified according to a known procedure(see, Landon, E. J. et al., Biochemical Pharmacology, 35, 4, 697–705, 1986), and the protocol may be described in brief as follows.

A. The Test Animal

Mice(ICR, male, 27~35 g) as the test animal were allowed in a condition of temperature 22±1° C. and relative humidity 60±5%. Feed and water were provided with no restriction while light and darkness were changed at an interval of 12 hours.

B. Administration of Drugs

The compound of the present invention was suspended in a solvent corn oil, and this suspension was administered in a dose of 10 ml/kg. Each group included 8 test animals, and the test compound was orally administered once per animal. After 1 hour from the administration of the test compound, thioacetamide solution(concentration: 90 mg/ml) in physiological saline was intraperitoneally injected in a dose of 1 ml/kg. As the control compounds, silymarin and DDB were selected.

C. Serum Collection and Biochemical Analysis

The test animals were provided with no feed and sufficient water for 24 hours from the administration of thioacetamide. Then, the test animals were put under slight anesthesia and their abdomens were opened in order to take blood from the inferior vena cava. This blood was centrifuged to obtain sera. ALT and AST values in the sera were measured using blood chemistry analyzer(Vitalab, Selectra II, Merck). The statistical significance for the test result of each group was examined based on Student's t-test, and the result was recognized as having a statistical significance when its P value is less than 5%.

When the typical compounds are orally administered to mice, the inhibitory effects thereof against liver injuries caused by thioacetamide are summarized in the following Table 5.

TABLE 5

Inhibitory Effect against Liver Injuries caused by Thioacetamide in Mice

| Compound | Dose(mg/kg) | Administration Route | Inhibitory Effect against Liver Injuries(%) | |
|---|---|---|---|---|
| | | | AST | ALT |
| Silymarin | 50 | p.o | −19 | −74 |
| DDB | 50 | p.o | −4 | 21 |
| Compound 1 | 50.0 | p.o | — | 99 |
| Compound 9 | 50.0 | p.o | — | 29 |
| Compound 13 | 50.0 | p.o | — | 91 |
| Compound 21 | 16.7 | p.o | 37 | 54 |
| | 50.0 | p.o | 98 | 98 |
| Compound 28 | 16.7 | p.o | 89 | 76 |
| | 50.0 | p.o | 94 | 87 |

Experimental Example 4
Inhibitory Effect Against Liver Injuries Caused by D-galactosamine/lipopolysaccharide The hepatoprotective effect of the compound of the present invention was identified according to a known procedure(see, Koji Hase et al., Biol. Pharm. Bull., 20, 4, 381–385, 1997), and the protocol may be described in brief as follows.

A. The Test Animal

Mice(ICR, male, 27~35 g) as the test animal were allowed in a condition of temperature 22±1° C. and relative humidity 60±5%. Feed and water were provided with no restriction while light and darkness were changed at an interval of 12 hours.

B. Administration of Drugs

The compound of the present invention was suspended in a solvent corn oil, and this suspension was administered in a dose of 10 ml/kg. Each group included 10 test animals, and the test compound was orally administered once per animal. After 1 hour from the administration of the test compound, D-galactosamine and lipopolysaccharide each of which dissolved in physiological saline were intraperitoneally injected at the same time in doses of 800 mg/kg and 10 μg/kg, respectively. As the control compounds, SY-640[N-methyl-N-(3,4-methylenedioxyphenacyl)acetamide; EP0350251], silymarin and DDB were selected.

C. Survival Rate

After the administration of D-galactosamine/lipopolysaccharide to the test animals, the test animals were observed for 24 hours to determine the lethality. The statistical significance for the test result of each group was examined based on Student's t-test, and the result was recognized as having a statistical significance when its P value is less than 5%.

When the typical compounds are orally administered to mice, the inhibitory effects thereof against fulminant liver injuries caused by D-galactosamine/lipopolysaccharide are summarized in the following Table 6.

TABLE 6

Inhibitory Effect against Fulminant Liver Injuries caused by D-galactosamine/lipopolysaccharide in Mice

| Compound | Dose(mg/kg) | Survival Rate (%) |
|---|---|---|
| Control | — | 30 |
| Silymarin | 50 | 90 |
| DDB | 50 | 80 |
| SY-640 | 50 | 90 |
| Compound 1 | 50 | 90 |
| Compound 9 | 50 | 90 |
| Compound 13 | 50 | 90 |
| Compound 21 | 5.6 | 100 |
| Compound 28 | 5.6 | 100 |

Experimental Example 5
Acute Toxicity Test

The purpose of the acute toxicity test is to determine the short-term toxicity of the test compound qualitatively and quantitatively when the compound is administered to the test animals.

In the present example, the acute toxicity test was performed using mouse as the test animal by referring to the standard of drug toxicity test based on the Notice No. 94-3 of National Institute of Safety Research. That is, mice(4 weeks old, ICR, male, SPF) received from Daehan Experimental Animal Center were used after they were adapted to the lab environment for 1 week. Feed and water were provided with no restriction except for the fasting period before the test.

Mice were fasted from 6 p.m. of the previous day to 9 a.m. of the day on which the test compound was administered. The compounds were ground and suspended in corn oil and then administered to the test animals in doses of 250 mg/kg, 500 mg/kg, 1,000 mg/kg, and 2,000 mg/kg, respectively. At this time, the administration volumes were 10 ml or 20 ml per body weight kg of mouse. Each group included 5 test animals. The test compound was formulated on the test date, and it was orally administered once using a syringe for oral administration. After the administration, the test animals were observed for 2 weeks. Clinical symptoms once a day and body weight three times a week were recorded. Further, autopsy was carried out after the period of observation in order to record any gross lesion.

From the results of acute toxicity test for the typical compounds according to the present invention, it can be seen that the lethality is 0% at the dose of up to 2000 mg/kg.

What is claimed is:

1. A pharmaceutical composition for the hepatoprotection and treatment of liver diseases comprising as an active ingredient a dihydroxyphenyl derivative represented by the following formula (1), pharmaceutically acceptable acid addition salt or stereochemical isomer thereof together with a pharmaceutically acceptable inert carrier:

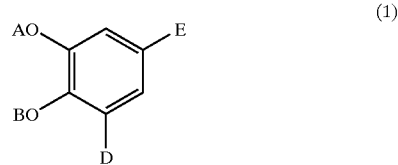

(1)

in which
A and B both represent hydrogen, or together represent a methylene group, D represents hydrogen or $C_1$–$C_4$-alkoxy, E represents the following substituent (a-1)

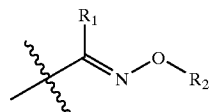

(a-1)

wherein $R_1$ represents hydrogen, $C_1$–$C_4$-alkyl or N-acetylmethylaminomethyl, $R_2$ represents hydrogen, or represents $C_1$–$C_4$-alkyl which is optionally substituted by hydroxycarbonyl, phenyl or 5- or 6-membered heteroaryl containing one or more hetero atoms selected from a group consisting of nitrogen and sulfur, wherein the heteroaryl can be substituted by $C_1$–$C_4$-alkyl, provided that when A and B together form a methylene group, D is hydrogen, $R_1$ is hydrogen, and $R_2$ is not hydroxycarbonylethyl; and provided that when A, B, D and $R_1$ independently are hydrogen, $R_2$ is not hydrogen.

2. The composition of claim 1 wherein the inert carrier is one or more selected from a group consisting of lactose, starch, mannitol and cottonseed oil.

3. A method for protecting liver and treating liver diseases comprising administering a pharmaceutical composition of claims 1 or 2 to a patient.

* * * * *